United States Patent
Wei et al.

(10) Patent No.: US 12,031,986 B2
(45) Date of Patent: *Jul. 9, 2024

(54) POLYPEPTIDE FOR TARGETING RECOGNITION OF IMMUNE CELLS AND APPLICATION THEREOF

(71) Applicant: KEYANGLE LIFE TECHNOLOGY CO., LTD., Guangdong (CN)

(72) Inventors: Yuan'an Wei, Guangdong (CN); Xueshu Liu, Guangdong (CN)

(73) Assignee: Keyangle Life Technology Co., Ltd., Guangdong (CN)

( * ) Notice: Subject to any disclaimer, the term of this patent is extended or adjusted under 35 U.S.C. 154(b) by 252 days.

This patent is subject to a terminal disclaimer.

(21) Appl. No.: 16/978,405

(22) PCT Filed: Jul. 25, 2019

(86) PCT No.: PCT/CN2019/097654
§ 371 (c)(1),
(2) Date: Sep. 4, 2020

(87) PCT Pub. No.: WO2021/012251
PCT Pub. Date: Jan. 28, 2021

(65) Prior Publication Data
US 2023/0176053 A1    Jun. 8, 2023

(51) Int. Cl.
*G01N 33/569* (2006.01)
*C12N 9/12* (2006.01)
*C12N 9/88* (2006.01)
*G01N 33/535* (2006.01)

(52) U.S. Cl.
CPC ..... *G01N 33/56972* (2013.01); *C12N 9/1205* (2013.01); *C12N 9/88* (2013.01); *C12Y 207/01028* (2013.01); *C12Y 406/01015* (2013.01); *G01N 33/535* (2013.01); *G01N 2333/912* (2013.01); *G01N 2333/988* (2013.01)

(58) Field of Classification Search
CPC .... C07K 2319/01; C12N 9/1205; C12N 9/88; C12Q 1/485; C12Q 1/527; C12Y 207/01028; C12Y 207/01029; C12Y 406/01015; G01N 2333/912; G01N 2333/988; G01N 33/535; G01N 33/56972
See application file for complete search history.

(56) References Cited

FOREIGN PATENT DOCUMENTS

| | | |
|---|---|---|
| CN | 109207451 A | 1/2019 |
| CN | 110885805 A | 3/2020 |
| WO | 2010/009368 A2 | 1/2010 |

OTHER PUBLICATIONS

Cabezas, et al., "Identification of human and rat FAD-AMP lyase (cyclic FMN forming) as ATP-dependent dihydroxyacetone kinases", Biochemical and Biophysical Research Communications 338 (2005) 1682-1689.

Cabezas, et al., UniProtKB/Swiss-Prot:Q3LXA3.2, retrieved from https//:www.ncbi.nlm.gov/protein/Q3LXA3.2 on Aug. 19, 2020.

Diao, et al., "Negative regulation of MDA5—but not RIG-I-mediated innate antiviral signaling by the dihydroxyacetone kinase", PNAS, vol. 104, No. 28, Jul. 10, 2007, 11706-11711.

Rodrigues, et al., "Bifunctional Homodimeric Triokinase/FMN Cyclase Contribution of Protein Domains To the Activities of the Human Enzyme and Molecular Dynamics Simulation of Domain Movements", the Journal of Biological Chemistry, vol. 289, No. 15, pp. 10620-10636, Apr. 11, 2014.

English translation of Written Opinion issued to PCT/CN2019/097654 dated Apr. 23, 2020.

*Primary Examiner* — Galina M. Yakovleva
(74) *Attorney, Agent, or Firm* — Hoffmann & Baron, LLP

(57) ABSTRACT

The present disclosure relates to a polypeptide recognizing immune cells, the polypeptide includes the following amino acid sequences: (a) an amino acid sequence containing C-terminal fragment sequence AILEVLQS of human Triokinase/FMN cyclase and its homologous sequence; or (b) an amino acid sequence that is substantially identical to the amino acid sequence described in (a), the substantially identical means 70% or more sequence identity to the amino acid sequence described in (a). The present invention also relates to a nucleic acid sequence encoding the polypeptide; a polypeptide probe used for targeting recognition of immune cells and containing the polypeptide described above and a reporter; a kit containing the probe described above; and, related applications of the polypeptide or probe described above.

14 Claims, 18 Drawing Sheets
Specification includes a Sequence Listing.

A.

DQPDPGAVAAAAILRAILEVLQSQGA

| | | Species |
|---|---|---|
| DQPDPGAVAAAAILRAILEVLQSQGA | | Bos taurus |
| DQPDPGAVAAAAILRFILEVLQSQGV | | Canis lupus |
| LQPDPGAVAAAAVLRIVLEGLQG | | Gallus gallus |
| EQPDPGAVAAAAILRAILEVLQS | | Homo sapiens |
| DQPDPGAVAAAAPRAILEVLQTQGA | | Mus musculus |
| DQPDPGAVAAAAFRAILEVLQTKAA | | Rattus norvegicus |
| DQPDPGAVAAAAILRAILEVLQSQGA | | Sus scrofa |

POLYPEPTIDE FOR TARGETING RECOGNITION OF IMMUNE CELLS AND APPLICATION THEREOF

CROSS-REFERENCE TO RELATED APPLICATIONS

The present application is a National Stage Application claiming the priority of co-pending PCT Application No. PCT/CN2019/097654 filed Jul. 25, 2019. The priority application is herein specifically incorporated by reference in its entirety.

SEQUENCE LISTING

The instant application contains a Sequence Listing encoded in text format which was filed electronically by EFS-web and is hereby incorporated by reference in its entirety. Said txt format Sequence Listing, created on Feb. 19, 2024, is named "2234-4 PCTUS Amended SEQ LISTING" and is 13,637 bytes in size.

TECHNICAL FIELD

The present disclosure relates to the fields of molecular biology, as well as cell detection and imaging. In particular, the present disclosure relates to a type of polypeptides for targeting recognition of immune cells, to a probe or a kit containing the polypeptide, and to a method for immunolabeling.

BACKGROUND

Immune cells mediate immune responses within the body, and include many different types of cells. These cells circulate throughout the blood and lymphatic systems and can be recruited to damaged tissue and sites of infection. Different types of immune cells are classified according to their functions and morphology. Most of the immune cells originate from hematopoietic stem cells and follow different pathways to develop and differentiate by responding to internal and external signals of the cell. From the classic immunological view, it believes that the mononuclear phagocytic system is a bone marrow-derived myeloid cell population, in which monocytes circulate in blood, bone marrow; and spleen without steady proliferation, then it differentiate into macrophages after leave blood and enter tissues. Macrophages are inherent phagocytes in lymphatic and non-lymphatic tissues and are considered to involve in tissue homeostasis by eliminating apoptotic cells and producing growth factors. However, the phenotypes, homeostatic cycles, and functions of these cells in different tissues can show very obvious heterogeneity (Geissmann et al., Development of monocytes, macrophages and dendritic cells, Science. 2010 Feb. 5: 327(5966): 656-61). This type of cells plays many different roles in normal tissue development, homeostasis, tissue repair, and immune response against pathogens. Mature monocytes/macrophages have high motility in vivo. In tissues, after phagocytosing bacteria, pathogens and dead cells, monocytes/macrophages can enter lymph-nodes or organs, such as spleen, through neighbouring lymph vessels, and present antigens to other lymphocytes, such as T or B cells.

It has been discovered in recent years that macrophages in many adult tissues originate from embryonic development stages, rather than from circulating monocytes. Many tissues have macrophages derived from embryo and circulating monocytes (also known as circulating macrophages or adult macrophages). These two types of macrophages form macrophage populations in adult tissues. This new understanding of macrophages within tissues has arisen a re-examination of the function of circulating monocytes. The inflammatory responses can trigger monocytes to differentiate into macrophages, however, it is unclear whether resident and newly recruited macrophages perform the same function during the inflammatory responses. As a result, macrophages may be activated to transform to different subpopulations and express different surface markers in different anatomic sites, or even in the same anatomic site, due to different origins and different environmental stimulations produced by the tissue microenvironment. Thus, it would be difficult to use, or give contradictory results by use of single biomarker antibody to identify different subpopulations of macrophages. For example, in experiments using Kumming mice as the animal model, better results can be obtained by using F4/80, CD11c, and CD68 antibodies to identify peritoneal, alveolar, and abdominal wall macrophages, respectively.

On the other hand, due to the wide-distribution and multi-functions, in vivo identification and imaging of a wide range of monocytes/macrophages, such as performing molecular imaging on abdominal cavity, respiratory tract, intestine, whole organs, muscle tissues, and the like, can provide intuitive and sensitive information at the cellular and molecular levels on the changes and the development of the immune system in an organism, in addition to the occurrence and development of inflammation and tumorigenesis. Undoubtedly, imaging of monocyte/macrophages populations is very important to obtain an accurate diagnosis of diseases. To achieve this, a broad-spectrum monocyte/macrophage recognition probe is needed.

The macrophages within tissues, especially alveolar macrophages, are different from other types of macrophages. Alveolar macrophages reside on the epithelial surface of alveoli and are in directly contact of and interactions with foreign objects, including directly inhaled airborne dust particles, bacteria, viruses, and the like. Whether or not alveolar macrophages can function properly is important to pulmonary immunity and inflammation treatments (see Sessile alveolar macrophages modulate immunity through connexin 43-based epithelial communication, Kristin Westphalen et al. Nature, 2014 Feb. 27: 506(7489): 503-506).

At the same time, alveolar macrophage is also an important targeting cell for pulmonary drug delivery research. The pulmonary drug delivery systems have the characteristics of rapid drug absorption and higher bioavailability, no first-pass effect of the liver, fewer metabolizing enzymes in the lung, low chemical and enzymatic degradations, and thus are especially suitable for drug delivery of proteins, nucleic acids and other bio-macromolecules drugs. In this regard, polypeptide probes and drug delivery carriers with specific targeting, non-toxic and fast metabolizable features are the most preferred. Therefore, it would have promising application aspects in many fields to use broad-spectrum molecular imaging probes, which target monocytes/macrophages, for imaging monocytes/macrophages in vivo or functioning as a drug delivery vehicle.

Currently, both in vivo and in vitro identification and imaging of monocytes/macrophages mostly use the corresponding antibodies to recognize various biomarkers or receptors of cells for identification and labeling. Based on this, a variety of histoimmunology and cellular immunology methods, which use primary antibodies in combination with secondary antibodies or use direct-labeled antibodies, has been developed. However, because antibodies are macromolecular proteins, their preparation and production involve a series of complex steps. During the preparation and production processes, there are many factors that may affect the activities of antibodies, resulting in the fact that the quality of the antibodies is unstable, and has great fluctuations from batch to batch. There is no uniform standard for the quality of the same antibody sold by different manufacturers. In addition, when fluorescent staining and labeling of monocytes/macrophages are carried out in vivo, the antigen-antibody binding and labeling could encounter challenges such as short fluorescence maintenance time.

Compared to proteins or antibodies, polypeptides do not exhibit a strictly three-dimensional active structure as those of proteins, and have low immunogenicity. Polypeptides are easy to be obtained through chemical synthesis, and are able to endure relatively stringent chemical modification and labeling while maintaining their activities. In addition, polypeptides have high affinity, easier penetration through tissues, and faster plasma clearance rates. Better pharmacokinetic properties can be achieved through modification of peptide structures.

Molecular imaging emerged in the early 21st century, since then it has been widely used in life sciences, medical researches, drug development, and other fields because it was easy to use and gave direct and sensitive results. Currently, molecular imaging technology has been developed to include Optical Imaging (OI), Magnetic Resonance Imaging (MRI), Radionuclide Imaging, and others, for example, Positron Emission Tomography (PET) and Single Photon Emission Computed Tomography (SPECT) and so on. However, each modality imaging method has its own advantages and disadvantages, and multi-modality imaging where multiple imaging technologies are jointly used will be the trend of future development. The in vivo molecular imaging technology of mammals allows researchers to directly monitor cell activity and molecular change behaviors within living organisms. However, the most important part for in vivo molecular imaging is the preparation of an appropriate in vivo targeting recognition probe.

Therefore, there is a need to provide a new targeted probe suitable for recognizing monocytes/macrophages for in vivo imaging or targeted drug delivery.

SUMMARY

To achieve the objective described above, the present disclosure provides a polypeptide for recognition of monocytes/macrophages in broad-spectrum, which can automatically and specifically recognize and adhere to macrophages residing in different anatomic sites in vivo. If the polypeptide is linked to an imaging reporter, it can carry out in situ imaging of different types of monocytes/macrophages, and clearly display the in vivo distribution and temporal-spatial relationship of monocytes/macrophages. On this basis, one can study the physiological functions and real-time distribution of monocytes/macrophages in vivo. If the polypeptide is linked to a drug molecule, the drug-polypeptide can serve as a targeted drug delivery system, thereby providing an effective tool for targeted drug delivery.

Therefore, one of the purposes of the present disclosure is to provide a novel functional polypeptide that can realize targeting recognition of immune cells, especially monocyte precursors and monocytes/macrophages.

Another purpose of the present disclosure is to provide a nucleic acid sequence encoding the polypeptide described above.

Yet another purpose of the present disclosure is to provide a probe containing the polypeptide described above for detecting monocyte precursors and monocytes/macrophages.

Yet another purpose of the present disclosure is to provide a kit containing the probe described above.

Yet another purpose of the present disclosure is to provide a method for immune cell labeling using the probe described above.

Yet another purpose of the present disclosure is to provide use of the polypeptide or probe described above in preparation of a reagent for in vivo imaging.

Yet another purpose of the present disclosure is to provide a targeted drug delivery system, which comprises the polypeptide described above and a drug molecule linked to the polypeptide.

Yet another purpose of the present disclosure is to provide use of the polypeptide described above in preparation of a targeted drug delivery carrier.

In one aspect of the present disclosure, the polypeptide for targeting recognition of immune cells comprises: (a) an amino acid sequence containing the C-terminal fragment AILEVLQS (SEQ ID NO.: 1) of human Triokinase/FMN cyclase: or (b) an amino acid sequence that is substantially identical to the amino acid sequence described in (a), wherein the term "substantially identical" refers to having 70% or more sequence identity to the amino acid sequence described in (a).

Further, the amino acid sequence described in (a) may be AILEVLQS (SEQ ID NO.: 1), LRAILEVLQS (SEQ ID NO.: 2), ILRAILEVLQS (SEQ ID NO.: 3), AAILRAILEVLQS (SEQ ID NO.: 4), EQPDPGAVAAAAILRAILEVLQS (SEQ ID NO.: 5), PGAVAAAAILRAILEVLQ (SEQ ID NO.: 6) or TKNMEAGAGRASYISSARLEQPDPGAVAAAAILRAILEVLQS (SEQ ID NO.: 7).

Further, the amino acid sequence of (b) which is substantially identical to the amino acid sequence defined above in (a), refers to an amino acid sequence obtained through modification, substitution or deletion of one or more amino acids in the amino acid sequence described above in (a). The specific method for the modification, substitution, or deletion may be any method known in the prior art.

Further, the amino acid sequence described in (b) is a sequence contained in a C-terminal fragment of a non-human Triokinase/FMN cyclase and has 70% or more sequence identity to the amino acid sequence described in (a).

Preferably, the amino acid sequence described in (b) has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence described in (a).

More preferably, the amino acid sequence described in (b) may be AVLEVLQG (SEQ ID NO.: 8), VLRAVLEVLQG (SEQ ID NO.: 9), EQPDPSAVAAAAILRAILEVLQG (SEQ ID NO.: 10), LQPDPSAVAAAAVLRAVLEVLQG (SEQ ID NO.: 11), LQPDPGAVAAAAVLRAVLEGLQG (SEQ ID NO: 12), DQPDPGAVAAAAIFRAILEVLQT-KAA (SEQ ID NO.: 13), DQPDPGAVAAAAILRTIL-EVLQSQGV (SEQ ID NO.: 14), DQPDPGAVAAAAIL-RAILEVLQSQGA (SEQ ID NO.: 15), or EQPDPGAVAAAAILRAILEVLQS (SEQ ID NO.: 16).

Further, the immune cells described herein may comprise lymphocytes, dendritic cells, monocyte precursors, monocytes/macrophages, basophils, eosinophils, and mastocytes, preferably monocyte precursors and monocytes/macrophages.

As used herein, the term "Triokinase/FMN cyclase" means an enzyme which is capable of catalyzing the phosphorylation of dihydroxyacetone and glyceraldehydes, and the cleavage of ribonucleosidediphosphate-X compounds (in which FAD is the optimal substrate), and can inhibit IFIH1-mediated cellular antiviral response (Negative regulation of MDA5—but not RIG-I-mediated innate antiviral signaling by the dihydroxyacetone kinase, Feici Diao et al., Proc Natl Acad Sci USA. 2007 Jul. 10:104(28): 11706-11). Triokinase/FMN cyclase (also known as DAK protein) was first discovered in prokaryotic/eukaryotic microorganisms (B. Erni et al. Small Substrate, Big Surprise: Fold, Function and Phylogeny of Dihydroxyacetone Kinases, *Cell. Mol. Life Sci.* 2006, 63:890-900), and was reported to be able to catalyze the phosphorylation of dihydroxyacetone to produce dihydroxyacetone phosphate (Dha-P). The FAD-AMP lyase (also known as FMN cyclase) was found in rat liver extracts in 2005 and has homologous amino acid sequences with those of DAK proteins of microorganisms. It was further confirmed that DAK proteins have dual functions of kinases and cyclase.

In the Uniprot protein database, the latest name of the DAK proteins is Triokinase/FMN cyclase. The C-terminal fragment of Triokinase/FMN cyclase has been found to be highly conserved in animals, especially in mammals (including humans) (A. Cabezas et al., Identification of human and rat FAD-AMP lyase (cyclic FMN forming) as ATP-dependent dihydroxyacetone kinases, *Biochemical and Biophysical Research Communications,* 2005, 338: 1682-1689). As shown in FIG. 1A, the C-terminal fragments of the Triokinase/FMN cyclases are highly conserved among various animals, with high homology and similarity. In addition, it was found that the C-terminal fragments of the Triokinase/FMN cyclases in the Uniprot database have 100% sequence identity (see FIG. 1B) among 20 mammal species (comprising primates such as humans, orangutans, and monkeys). The coding gene of the human Triokinase/FMN cyclase is located on chromosome 11, region 11q12.2, with GenBank accession number DQ138290 and geneID: 26007 (also numbered as DKFZP586B1621).

However, none of the prior reports and art discloses or implies that Triokinase/FMN cyclase can recognize immune cells, or monocyte precursors and monocytes/macrophages. The present disclosure finds and verifies for the first time that a polypeptide containing a C-terminal fragment of Triokinase/FMN cyclase can specifically recognize immune cells, in particular, can specifically recognize monocyte precursors and monocytes/macrophages. This will greatly simplify the in vivo labeling or imaging process of monocyte precursors and monocytes/macrophages, and improve the imaging effect simultaneously.

According to some embodiments of the present disclosure, it was proved that a conserved amino acid sequence contained by the C-terminal fragments of the Triokinase/FMN cyclases in both humans and other animals (e.g., cows, dogs, and rats, etc.) has similar functions to the amino acid sequence of (a), i.e. can realize targeting recognition of immune cells, especially monocyte precursors and monocytes/macrophages.

In the present disclosure, there is no particular restriction on animal species. For example, birds and mammals can all be applied to the present disclosure. Examples of birds may comprise chickens, ducks, and other bird species: examples of mammals may comprise mice, rats, rabbits, pigs, dogs, cows, and primates.

It should be understood by those skilled in the art that the polypeptide in the present disclosure may be a polypeptide fragment from a natural protein, or be obtained by a well-known peptide synthesis method.

Further, the polypeptide according to the present disclosure may comprise 80 or less amino acid residues, preferably comprise 70, 60, 55, 50, 45, 44, 43, 42, 42, 41, 40 or less amino acid residues, more preferably, comprise 6 to 45 amino acid residues, and most preferably, comprise 8 to 42 amino acid residues. For example, the polypeptide according to the present disclosure may comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 amino acid residues. Further, the polypeptide according to the present disclosure may comprise a fragment of 80 or less amino acid residues from the C-terminal fragments of human or non-human Triokinase/FMN cyclases, or a site-directed modification-containing fragment thereof.

Further, the polypeptide of the present disclosure can specifically recognize immune cells, preferably specifically recognize monocyte precursors and monocytes/macrophages.

In another aspect of the present disclosure, a nucleic acid sequence encoding the polypeptide described above is provided.

In yet another aspect of the present disclosure, a probe for targeting recognition of immune cells is provided, the probe comprise of the polypeptide of the present disclosure described above and a reporter, wherein the reporter may be linked to the N- and/or C-terminal of the polypeptide.

The N- and/or C-terminal of the polypeptide of the present disclosure may be directly linked to a reporter. Alternatively, the C- or N-terminal of the polypeptide may be linked with one or more amino acid residues which have an easily modifiable side chain, and then further linked to a reporter. The amino acid residues which have an easily modifiable side chain may be, for example, cysteine (C) or lysine (K). It should be understood that there are no particular restriction to the linkage of the reporter with the polypeptide, and the reporter can be linked by any suitable method known in the prior art, preferably linked by covalent binding.

The reporter may be a chromogenic enzyme, a fluorescent labeling group, a chemiluminescent labeling group, an isotope, or a magnetic functional group.

The chromogenic enzyme can catalyze the conversion of a substrate into a colored compound, and may be, for example, peroxidase, alkaline phosphatase, and the like.

The fluorescent labeling group may be ones commonly used in the art, and be a fluorescent group such as fluorescent protein, rhodamine, fluorescein, anthocyanin dye, cyanine dye (e.g., near-infrared cyanine dyes), AlexaFluor® dye, nanoparticles, and/or quantum dots (Huang Zhiping et al., Application of polypeptide fluorescent probes in protein detection, *Chinese Science: Chemistry,* 2013, Volume 43, Issue 8: 1013-1021). For example, the fluorescent labeling group may be carboxyfluorescein (FAM), fluorescein thiocyanate (FITC), dansyl chloride, 2,4-dinitrobenzene, carboxyrhodamine 110, Texas redR, pentamethine cyanine dye (Cys5R), heptamethine cyanine dyes (Cys7®), green fluorescent protein (GFP), enhanced green fluorescent protein (EGFP), red fluorescent protein (RFP), and the like.

Further, the magnetic functional group may be a group capable of magnetic resonance imaging and changing relaxation efficiency, and preferably be a paramagnetic group, such as chelate of gadolinium or manganese, ultra-small paramagnetic or superparamagnetic nanoparticles (e.g., iron oxide magnetic nanoparticles, specifically an imaging reporter for magnetic resonance imaging using iron trioxide or ferroferric oxide magnetic nanoparticles and the like).

Further, the isotope may be radionuclide, such as radionuclide used in positron emission tomography (PET), single photon emission computed tomography (SPECT) and other imaging processes. For example, the isotope may be one or more selected from $^{11}C$, $^{13}N$, $^{15}O$, $^{18}F$, $^{75}Br$, $^{76}Br$, $^{32}P$, $^{35}S$, $^{122}I$, $^{124}I$, $^{62}Cu$, $^{64}Cu$, $^{68}Ga$, $^{86}Y$, $^{99}mTc$, $^{123}I$, $^{125}I$, $^{111}In$, $^{201}Tl$ and the like.

Further, the probe can achieve targeting recognition of immune cells, preferably lymphocytes, dendritic cells, monocyte precursors, monocytes/macrophages, basophils, eosinophils and mastocytes, and more preferably monocyte precursors and monocytes/macrophages.

Further, the probe may be used for in vivo imaging in mammals. Preferably, the probe may be used for in vivo imaging, and more preferably, be used for targeted imaging of pulmonary macrophages.

Further, the probe may be used for in vitro immunostaining and/or microscopic analysis of cells or tissues. For example, the probe may be used for in vitro immune cell labeling and microscopic analysis for cultured cells, tissue sections, smear examination, or cell-climbing slices. Preferably, the probe may be used for in vitro staining of cultured monocyte precursors and monocyte/macrophages, or for staining or microscopic analysis of monocyte precursors and monocyte/macrophages from tissue sections, smears, and cell-climbing slices.

Another aspect of the present disclosure is to provide a method for in vivo imaging in mammals, using an effective amount of the probe described above. For example, the probe may be injected into a living body by a method commonly used in the art for in vivo imaging.

In yet another aspect of the present disclosure, a kit containing the probe described above is provided. The probe may be in a liquid or solid form. The kit may further contain an initial solvent, a diluent, and operating instructions. The initial solvent may be DMSO, DMF and the like. The diluent may be phosphate buffer, cell culture medium and the like, for example, may be DMEM.

The kit is suitable for in vivo imaging of immune cells, preferably monocyte precursors and monocytes/macrophages. In addition, the kit also may be used for in vitro immunostaining and/or microscopic analysis of cells or tissues. For example, the kit may be used for immunostaining or microscopic analysis of cultured cells, tissue sections, smears, and cell-climbing slices.

In yet another aspect of the present disclosure, use of the polypeptide or probe described above in preparation of a kit for in vivo imaging of mammals is provided.

In yet another aspect of the present disclosure, it provides a composition containing the polypeptide described above as an active ingredient for imaging of immune cells, preferably for in vivo or in vitro imaging of monocyte precursors and monocytes/macrophages.

In yet another aspect of the present disclosure, it provides use of the polypeptide or probe described above in preparation of a reagent for in vivo imaging.

In yet another aspect of the present disclosure, it provides a targeted drug delivery carrier, which contains the polypeptide described above. The targeted drug delivery carrier of the present disclosure may further contain a drug linked to the polypeptide. The targeted drug delivery carrier of the present disclosure may be used for targeted drug delivery to immune cells, preferably monocyte precursors and monocytes/macrophages, and more preferably pulmonary macrophages.

In yet another aspect of the present disclosure, the probe described above may be incubated with cells to be labeled, tissue sections, smears, cell-climbing slices, or a living tissue for immunostaining.

In yet another aspect of the present disclosure, it provides use of the polypeptide described above in preparation of a targeted drug delivery carrier. The targeted drug delivery carrier of the present disclosure may be administered via subcutaneous injection, intravenous injection, intramuscular injection or pulmonary inhalation.

In yet another aspect of the present disclosure, it provides a method for convenient, oral and non-invasive in situ imaging or targeted drug administration for pulmonary immune cells. After spraying into the trachea of a mouse, the polypeptide or probe of the present disclosure can be diffused along the trachea in the living body, automatically target and aggregate in alveolar macrophages, and thus allow real-time and in situ imaging or targeted drug delivery to pulmonary and alveolar macrophages. The imaging may be maintained for more than 24 hours. The experiments of the present disclosure confirm that the probe described above can diffuse to lungs through mouth inhalation, and recognize macrophages therein, which is consistent with CD11c antibody recognizing alveolar macrophages. In addition, the present disclosure also found that no abnormal physiological activity of mice was observed in two weeks, after the probe described above was sprayed orally or tail-intravenously injected into the mice. This demonstrates that the polypeptide or probe of the present disclosure has less toxicity.

Since alveolar macrophages play an important role in lung immunity and treatment of pulmonary inflammation, the polypeptide or probe of the present disclosure can be used as a drug delivery carrier for delivering the drug to lung, particularly to alveolar macrophages, via oral administration route, with excellent targeting specificity and low toxicity.

As used therein, the term "targeting recognition" means that the polypeptide of the present disclosure specifically interacts with some immune cells, such as monocyte/macrophage.

Compared with commonly used antibody- or protein-based monocyte/macrophage recognition processes, the small molecular polypeptide of the present disclosure for targeting recognition of immune cells, such as monocyte/macrophages, have many advantages.

Firstly, the recognition of monocyte/macrophages by the small molecular polypeptide of the present disclosure would not be interfered by Fc receptor located on the surface of immune cells. Such recognition has no obvious tissue specificity. Thus, the polypeptide-based probe of the present disclosure can be used as a broad-spectrum immune cell recognition probe. For example, the polypeptide of the present disclosure can selectively recognize monocyte precursors, peritoneal macrophages and alveolar macrophages. Moreover, the polypeptide of the present disclosure has no obvious selectivity to the tissue-specific phenotypes of monocyte/macrophages. Somatic cells in the tissues are stained relatively less intensively compared to monocyte/macrophages. Therefore, the polypeptide of the present disclosure exhibits excellent selectivity on monocyte/macrophages.

Secondly, in a strict sense, the small molecular polypeptide of the present disclosure has no tertiary structure as those of proteins. The polypeptide sequences of the present disclosure are derived from natural triokinase/FMN cyclases of animals, and thus have low immunogenicity. Labeling in a living body substantially does not trigger immunogenicity, and would not lead to a severe immune response within the body. In addition, the polypeptide of the present disclosure has no cytotoxicity and has long-term signal retention in vivo. It is well known that the in vivo labeling avoids many disadvantages of in vitro labeling, such as damages to the structures of tissues and cell membranes by fixation staining method, and inability to observe intact cell. In addition, cells that have undergone in vivo staining can then be cultured and observed in vitro after elutriation, which is particularly suitable for creating novel animal models for living observation and for biological function researches of living cells.

Thirdly, the polypeptide of the present disclosure has high biocompatibility, easy penetration of tissues, and faster plasma clearance rate, and can exhibit better pharmacokinetic properties by appropriate structural modification.

Fourthly, the polypeptide of the present disclosure may link to a reporter with little effect on the activity of the polypeptide. The polypeptide can still maintain its activity after being subjecting to severe chemical modifications and labeling. Thus, the polypeptide, linked with the reporter, of the present disclosure can perform one-step labeling on living cells, cultured cells, tissue sections, smears, and cell-climbing slides.

Finally, the small molecular polypeptide or probe of the present disclosure can be easily obtained from chemical synthesis, and thus can be mass-prepared and produced, with accurately controlled quality.

Based on the above-mentioned advantages, the polypeptide or polypeptide-based probe of the present disclosure can be widely used to study the biological functions and activities of macrophages from cells and tissues of various animals, and can also be used for in vivo labeling, fluorescence or microscopic imaging, and the like. Based on the features of the polypeptide-based probe of the present disclosure, such as non-cytotoxicity, high sensitivity and efficiency, and selective staining, it provides a convenient and fast approach to perform direct fluorescent staining and other cell imaging processes on, for example, in vivo or ex vivo tissues, in vitro cultured cells, and the like.

BRIEF DESCRIPTION OF THE DRAWINGS

FIG. 1A shows that the C-terminal fragments of the Triokinase/FMN cyclases are highly conserved among different species. The first sequence DQPDPGAVAAAAIL-RAILEVLQSQGA (SEQ ID NO. 15) is compared to C-terminal fragments corresponding to SEQ ID NO: 18, 14, 12, 16, 17, 13 and 15 respectively. FIG. 1B shows that the C-terminal fragments of the Triokinase/FMN cyclase proteins have 100% sequence identity among 20 mammalian species. The first sequence KNMEAGAGRASYISSAR-LEQPDPGAVAAAAILRAILEVLQS (SEQ ID NO:19) is compared to C-terminal fragments corresponding to SEQ ID NO: 20, 21, 22, 23, 24, 25, 26, 27, 28, 29, 30, 31, 32, 33, 34, 35, 36, 37, 38 and 19, respectively.

FIG. 2A is an AK9-labeled image (shown in red in the original fluorescent color image); FIG. 2B is a F4/80-labeled image (shown in green in the original fluorescent color image); FIG. 2C is a nuclear stained image obtained by using Nucblue (shown in blue fluorescence in the original fluorescent color image); and FIG. 2D is a merged image of FIGS. 2A, 2B, and 2C.

FIG. 3A is a LK11-labeled image (shown in red in the original fluorescence color image): FIG. 3B is a nuclear-staining image obtained by using Nucblue (shown in blue in the original fluorescence color image): and FIG. 3C is a merged image of FIGS. 3A and 3B.

FIG. 4A is a labeled image obtained by using the AK14 fluorescent probe (shown in red in the original fluorescence color image): FIG. 4B is a nuclear-staining image obtained by using Nucblue (shown in blue in the original fluorescence color image): and FIG. 4C is a merged image of FIGS. 4A and 4B.

FIG. 6A is a fluorescent labeled image obtained by using the EK24 fluorescent probe (shown in red in the original fluorescence color image), and FIG. 6B is a nuclear-staining image obtained by using Nucblue (shown in blue in the original fluorescence color image), and FIG. 6C is a merged image of FIGS. 6A and 6B.

FIGS. 7A and 7B show fluorescent labeled images obtained by using EK24 probe and F4/80 antibody, respectively; and FIG. 7C is a merged image of FIGS. 7A and 7B.

FIG. 8A shows a direct fluorescently labeled image of macrophages from a rat abdominal cavity obtained by using the EK24 fluorescent probe: FIG. 8B shows a fluorescent labeled image of cultured macrophages isolated from rat peritoneal cavity with EK24 probe.

FIG. 12A is a labeled image obtained by using the EK24 fluorescent probe, and FIG. 12B is a nuclear-staining image obtained by using Nucblue, and FIG. 12C is a merged image of FIGS. 12A and 12B.

FIG. 13A is a fluorescent labeled image obtained by using the KS24 fluorescent probe (shown in red in the original fluorescence color image), FIG. 13B is a nuclear-staining image obtained by using Nucblue (shown in blue in the original fluorescence color image), and FIG. 13C is a merged image of FIGS. 13A and 13B.

FIGS. 14A, 14B, 14C, and 14D show fluorescent labeled images obtained by using the KS24 fluorescent probe to incubate for 10 min, 20 min, 40 min and 80 min, respectively. In each of FIGS. 14A, 14B, 14C, and 14D, i) is a KS24-labeled image (shown in red fluorescence in the original fluorescence color image), and ii) is a nuclear-staining image with Nucblue (shown as blue fluorescence in the original fluorescence color image), and iii) is a merged image of i) and ii).

FIG. 15A is a PK20-labeled image (shown in red fluorescence in the original fluorescence color image), and FIG. 15B is a nuclear-staining image with Nucblue (shown in blue in the original fluorescence color image), and FIG. 15C is a merged image of FIGS. 15A and 15B.

FIG. 16A is a TS42-labeled image (shown in green in the original fluorescence color image), and FIG. 16B is a nuclear-staining image with Nucblue (shown in blue in the original fluorescence color image), and FIG. 16C is a merged image of FIGS. 16A and 16B.

FIG. 17A is a LK24-labeled image (shown in red fluorescence in the original fluorescence color image), and FIG. 17B is a nuclear-staining image with Nucblue (shown in blue fluorescence in the original fluorescence color image), and FIG. 17C is a merged image of FIGS. 17A and 17B.

FIG. 18A is a r-KA27-labeled image (shown in red fluorescence in the original fluorescence color image), and FIG. 18B is a nuclear-staining image with Nucblue (shown in blue in the original fluorescence color image), and FIG. 18C is a merged image of FIGS. 18A and 18B.

FIG. 19A is a d-KV27-labeled image (shown in red fluorescence in the original fluorescence color image), and FIG. 19B is a nuclear-staining image with Nucblue (shown in blue fluorescence in the original fluorescence color image), and FIG. 19C is a merged image of FIGS. 19A and 19B.

FIG. 20A is a b-KA27-labeled image (shown in red fluorescence in the original fluorescence color image), and FIG. 20B is a nuclear-staining image with Nucblue (shown in blue in the original fluorescence color image), and FIG. 20C is a merged image of FIGS. 20A and 20B.

FIG. 21A is a KESG244-labeled image (shown in red in the original fluorescence color image), and FIG. 21B is a nuclear-staining image with Nucblue (shown in blue in the original fluorescence color image), and FIG. 21C is a merged image of FIGS. 21A and 21B.

FIG. 22A is a Cx-LK24-labeled image (shown in red fluorescence in the original fluorescence color image), and FIG. 22B is a nuclear-staining image with Nucblue (shown in blue in the original fluorescence color image), and FIG. 22C is a merged image of FIGS. 22A and 22B.

FIG. 23A is a EK24-labeled image (shown in red fluorescence in the original fluorescent color image), FIG. 23B is a CD68 antibody labeled image (shown in green in the original fluorescent color image), FIG. 23C is a nuclear-staining image with Nucblue (shown in blue in the original fluorescent color image), and FIG. 23D is a merged image of FIGS. 23A, 23B, and 23C.

FIG. 24A is an EK24-labeled image, and FIG. 24B is a CD11c-labeled image (shown in green in the original fluorescence color image), and FIG. 24C is a merged image of FIGS. 24A and 24B.

FIG. 25A is a Hx-AVGK9-labeled image (shown in red fluorescence in the original fluorescence color image), and FIG. 25B is a nuclear-staining image with Nucblue (shown in blue in the original fluorescence color image), and FIG. 25C is a merged image of FIGS. 25A and 25B.

FIG. 26A is an IK12-labeled image (shown in red fluorescence in the original fluorescence color image), and FIG. 26B is a nuclear-staining image with Nucblue (shown in blue in the original fluorescence color image), and FIG. 26C is a merged image of FIGS. 26A and 26B.

FIG. 27A is a Hx-VVGK12-labeled image (shown in red in the original fluorescence color image), and FIG. 27B is a nuclear-staining image with Nucblue (shown in blue in the original fluorescence color image), and FIG. 27C is a merged image of FIGS. 27A and 27B.

DETAILED DESCRIPTION

Hereafter, the present disclosure will be described in detail with reference to the specific embodiments. However, it should be understood that the present disclosure will not be limited to the following embodiments. The protection scope of the present disclosure is defined by the appended claims, and the following embodiments of the present disclosure can be arbitrarily changed and combined without departing from the scope of the present disclosure.

Example 1. Preparation of AK9 Fluorescent Probe

The polypeptides used herein were obtained by means of conventional solid phase peptide chemical synthesis using a CEM fully automated microwave peptide synthesizer according to operating instructions provided by the supplier. The polypeptides used herein were derived from the C-terminal fragment of human or non-human Triokinase/FMN cyclases.

In this example, the polypeptide having the following amino acid sequence was synthesized: AILEVLQSK (SEQ ID NO.: 39).

According to the manufacturer's instructions, the synthesized polypeptide was mixed with a reaction reagent of HOOK™ Dye Rhodamine Labeling Kit (Cat. #786-142, Biosciences), adjusted pH, reacted for 1-2 hours, purified by HPLC to obtain the AK9 fluorescence probe. The chemical structure of the obtained fluorescent probe is as follows:

AILEVLQS-Y (AK9), wherein, Y is a lysine+a fluorescent reporter which is a rhodamine fluorescent labeling group linked to an amino group on the side chain of lysine.

Example 2. Preparation of AK9 Fluorescent Probe Solution 1 mg of AK9 fluorescent probe was dissolved in 177 μL of DMSO (dimethyl sulfoxide), which was then added to 13981 μL serum-free DMEM (Hyclone) medium, mixing well to give 50 μM of AK9 fluorescent probe solution. As required, 50 μM of AK9 fluorescent probe solution can be diluted by adding serum-free DMEM medium during use.

Figure 1:
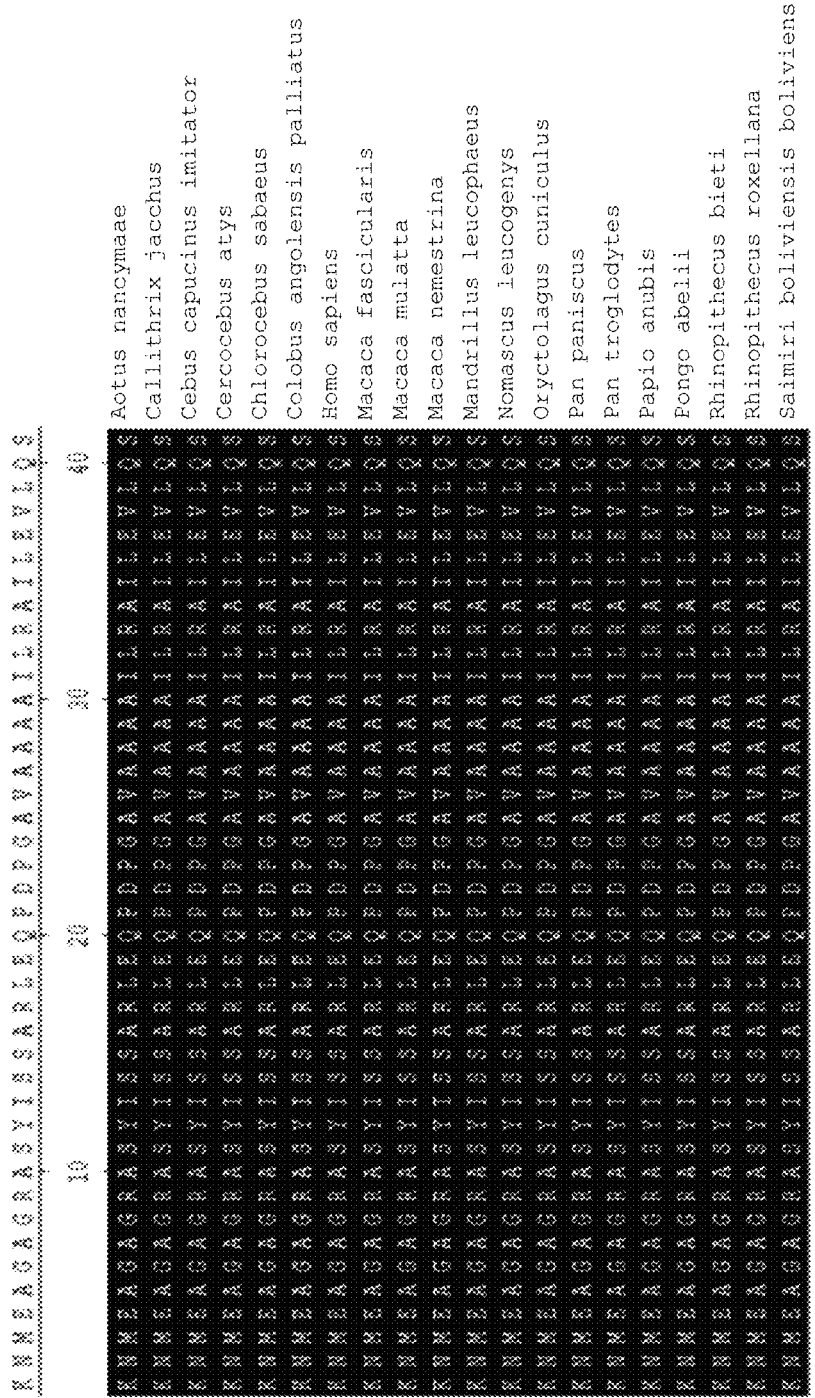
FIG. 1 shows the high homology of the C-terminal fragments of Triokinase/FMN cyclases among different animal species
Figure 2:
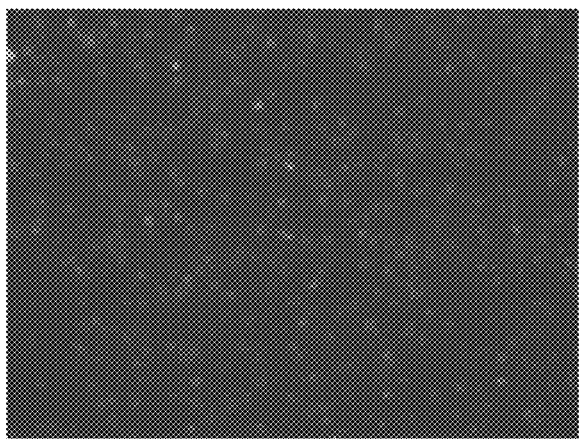
FIG. 2 shows in vivo fluorescent labeled images obtained by staining macrophages in a mouse abdominal cavity with AK9 fluorescent probe. Wherein the mouse peritoneal macrophages were first labeled with the AK9 fluorescent probe in vivo, and then removed from the mouse peritoneal cavity for F4/80 antibody and Nucblue labeling.
Figure 2:
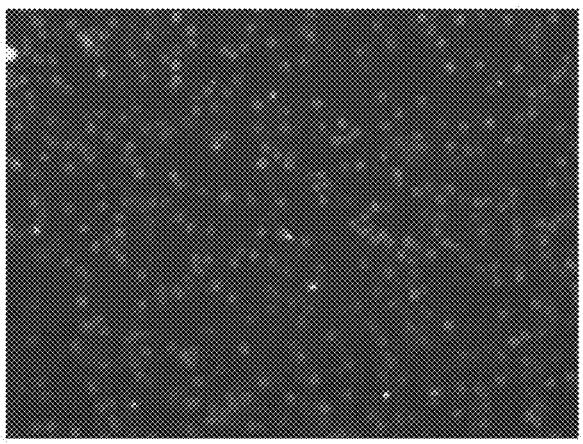
Figure 2:
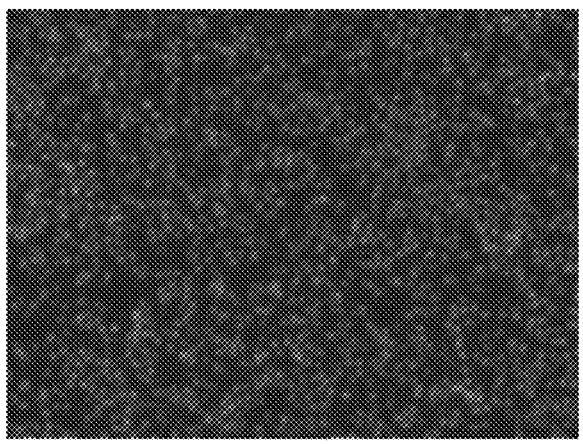
Figure 2:
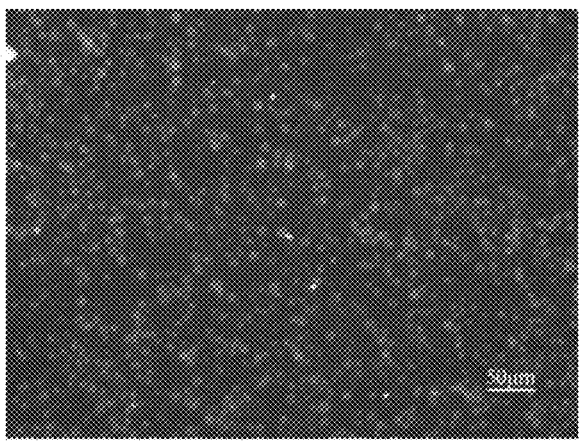

Example 3. In Vivo Fluorescent Labeling Macrophages in a Mouse Abdominal Cavity with the AK9 Fluorescent Probe Dilute 300 μL of 50 μM AK9 fluorescent probe solution with serum-free DMEM incomplete medium to obtain 1 mL of solution, then inject into the abdominal cavities of 5-8 week old Kunming mice. After 4 hours, inject 5 mL of 1×PBS, and massage. After 10 minutes, sacrifice the mice by cervical vertebra dislocation. Cut the abdominal cavity skin of the mice, pierce the abdominal wall muscle by syringe, and extract the fluid in the abdominal cavity of the mice. Centrifuge the extracted peritoneal fluid at 1000 rpm for 5 min, wash twice with 1×PBS. Double-stain an appropriate number of cells with Alexa Fluor 488 anti-mouse F4/80 antibody (Biolegend). Add the stained cells to a 96-well plate and stain with a nuclear dye Nucblue (Invitrogen). Observe under EVOS FL Auto fluorescence microscope (Life Technologies, 20×, light source 50%, exposure 200 ms, gain 10) after the suspended cells were settled down at the bottom of the plate. The results are shown in FIG. 2.

FIG. 2A is an AK9-labeled image (shown in red fluorescence in the original fluorescence color image).

FIG. 2B is a F4/80 antibody labeled image (shown in green fluorescence in the original fluorescent color image). F4/80 antigen is currently recognized as a membrane biomarker of mouse peritoneal macrophages.

FIG. 2C is a Nucblue-stained nuclear image (shown in blue fluorescence in the original fluorescence color image).

FIG. 2D is a merged image of FIGS. 2A, 2B, and 2C. From this figure, it can be seen that both the AK9 fluorescent probe and the F4/80 antibody are labeled on the same cells. This result indicates that cells labeled with F4/80 antibody are also labeled with the AK9 fluorescent probe, which confirms the AK9 fluorescent probe can targeting recognition of macrophages.

Example 4. Fluorescent Labeling of Macrophages by the Probes which are Derived from the C-Terminal Fragments of Triokinases/FMN Cyclases of Different Mammal Species Table 1 lists probes, which contain the polypeptide fragments from the C-terminal fragments of Triokinases/FMN cyclases of different species and were prepared by a similar process as described in Examples 1 and 2, and in vivo imaging results of mouse peritoneal macrophages using these probes.

TABLE 1

Probes from C-terminal fragments of Triokinases/FMN cyclases of different animal species and in vivo imaging results of mouse peritoneal macrophages using the probes.

Figure 3:
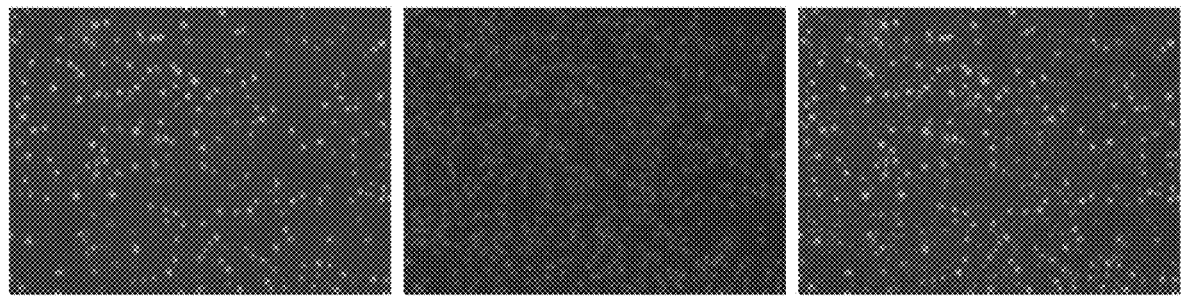
FIG. 3 shows in vivo fluorescent labeled images obtained by staining macrophages in a mouse abdominal cavity with LK11 fluorescent probe. Wherein the mouse peritoneal macrophages were first labeled with the LK11 fluorescent probe in vivo, and then removed from the mouse peritoneal cavity for Nucblue staining.
Figure 4:
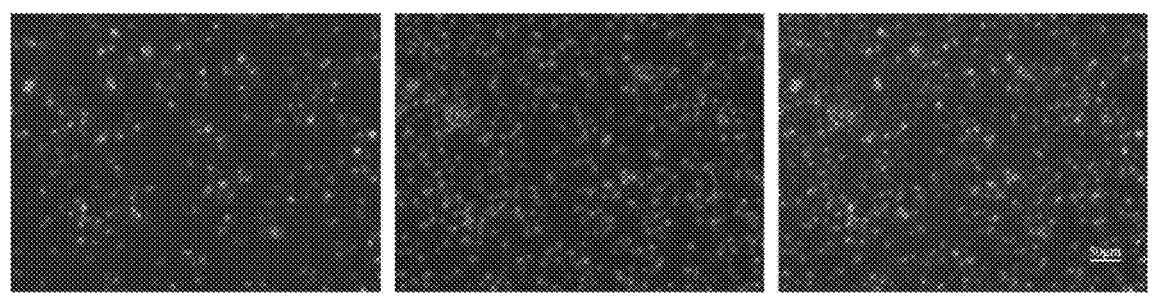
FIG. 4 shows in vivo fluorescent labeled images obtained by staining macrophages in a mouse abdominal cavity with AK14 fluorescent probe. Wherein the mouse peritoneal macrophages were first labeled with the AK14 fluorescent probe in vivo, and then removed from mouse peritoneal cavity for Nucblue staining.
Figure 11:
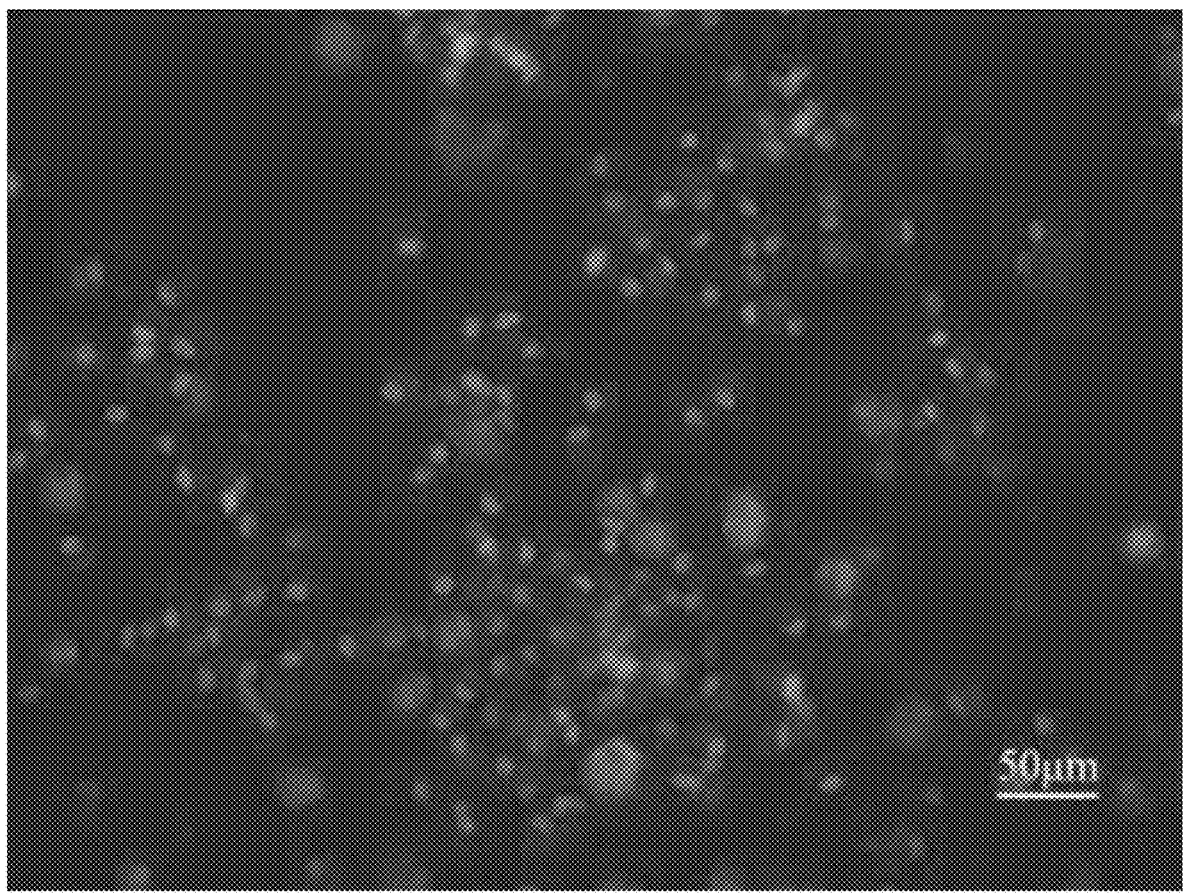
FIG. 11 shows a fluorescent labeled image obtained by staining cultured monocyte precursors isolated from New Zealand White Rabbit bone marrow; with EK24 fluorescent probe (shown in red in the original fluorescence color image) and Nucblue (shown in blue in the original fluorescence color image).
Figure 12:
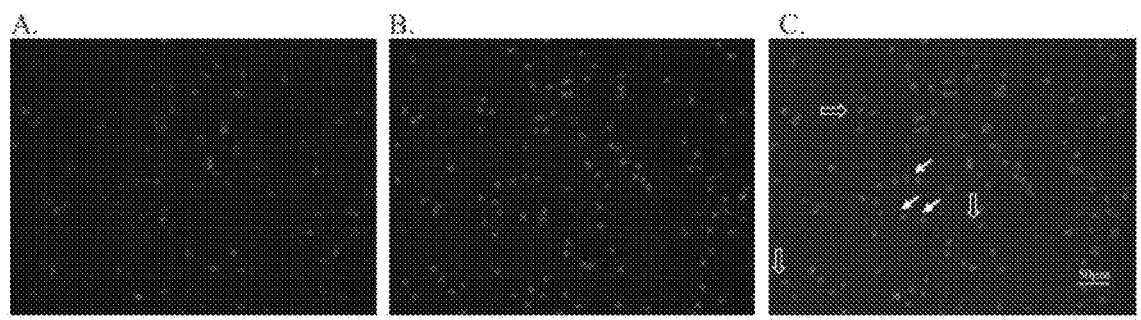
FIG. 12 shows fluorescent labeled images obtained by staining cultured peritoneal macrophages and other cells released from enzyme-digested mesenterium with EK24 fluorescent probe.
Figure 13:
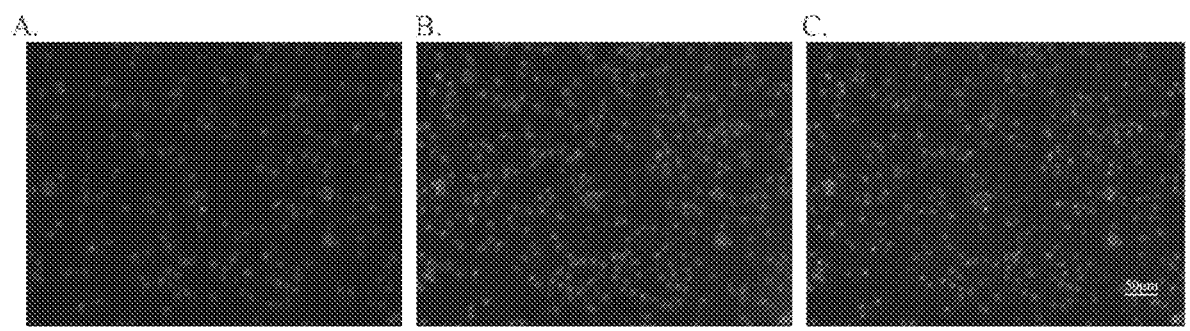
FIG. 13 shows in vivo fluorescent labeled images obtained by staining macrophages in a mouse abdominal cavity with KS24 fluorescent probe. Wherein the mouse peritoneal macrophages were first labeled with the KS24 fluorescent probe in vivo, and then removed from mouse peritoneal cavity for Nucblue staining.
Figure 14:
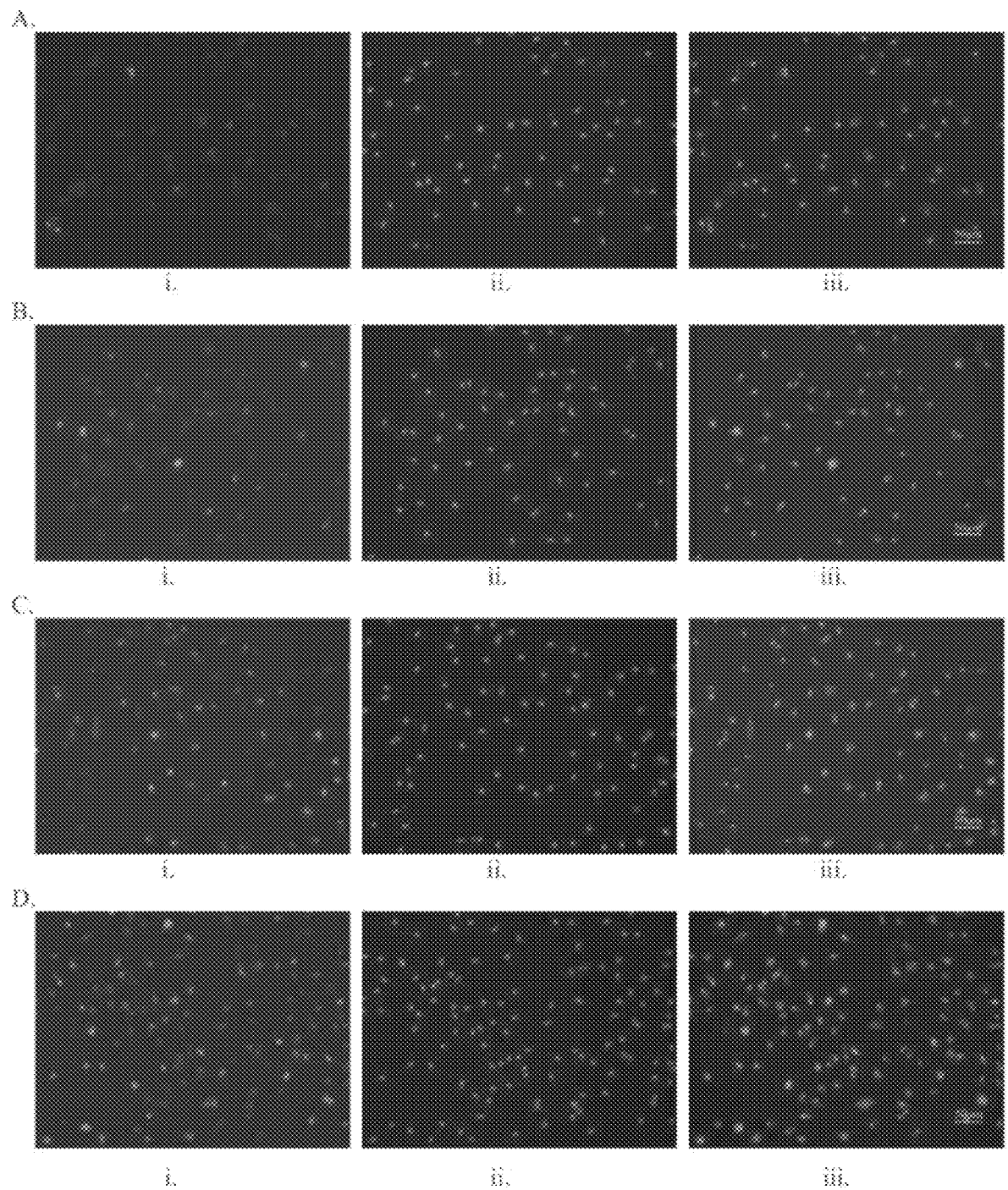
FIG. 14 shows the fluorescent labeled images obtained by staining mouse primary monocyte precursors with KS24 fluorescent probe at different incubation times.
Figure 15:
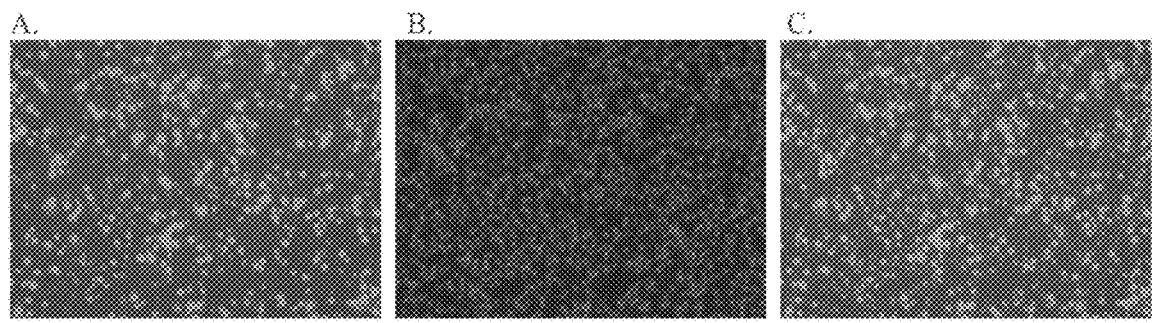
FIG. 15 shows in vivo fluorescent labeled images obtained by staining macrophages in a mouse abdominal cavity with PK20 fluorescent probe. The mouse peritoneal macrophages were first labeled with the PK20 fluorescent probe in vivo, and then removed from mouse peritoneal cavity for Nucblue staining.
Figure 16:
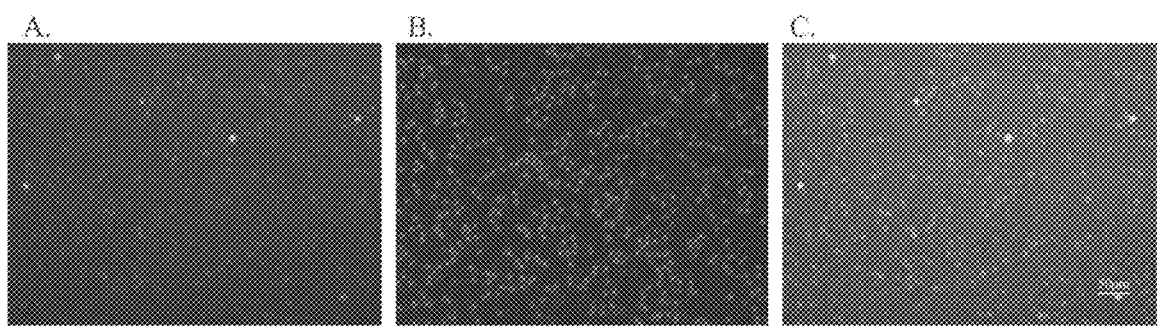
FIG. 16 shows in vivo fluorescent labeled images obtained by staining macrophages in a mouse abdominal cavity with TS42 fluorescent probe. The mouse peritoneal macrophages were first labeled with the TS42 fluorescent probe in vivo, and then removed from mouse peritoneal cavity for Nucblue staining.
Figure 17:
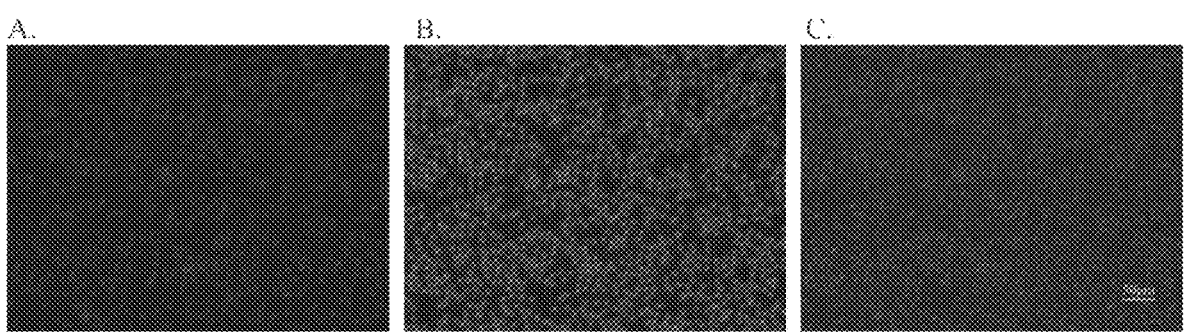
FIG. 17 shows in vivo fluorescent labeled image obtained by staining macrophages in a mouse abdominal cavity with LK24 fluorescent probe. Wherein the mouse peritoneal macrophages were first labeled with the LK24 fluorescent probe in vivo, and then removed from mouse peritoneal cavity for Nucblue staining.
Figure 18:
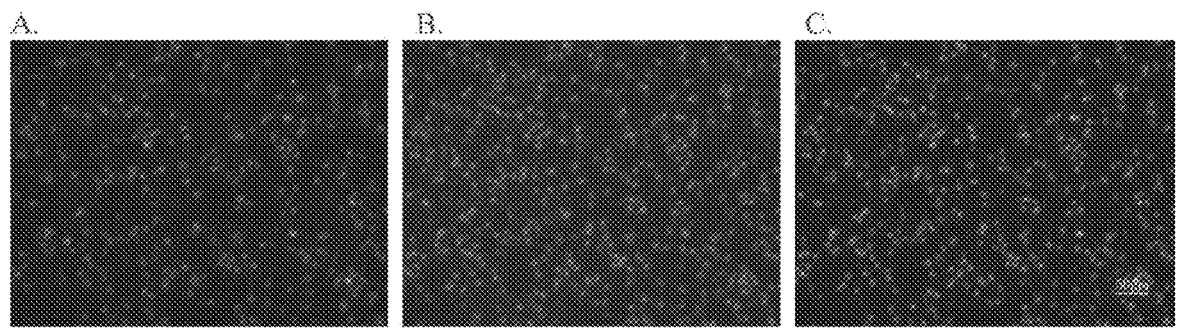
FIG. 18 shows in vivo fluorescent labeled image obtained by staining macrophages in a mouse abdominal cavity with r-KA27 fluorescent probe. Wherein the mouse peritoneal macrophages were first labeled with r-KA27 fluorescent probes in vivo, and then removed from mouse peritoneal cavity for Nucblue staining.
Figure 19:
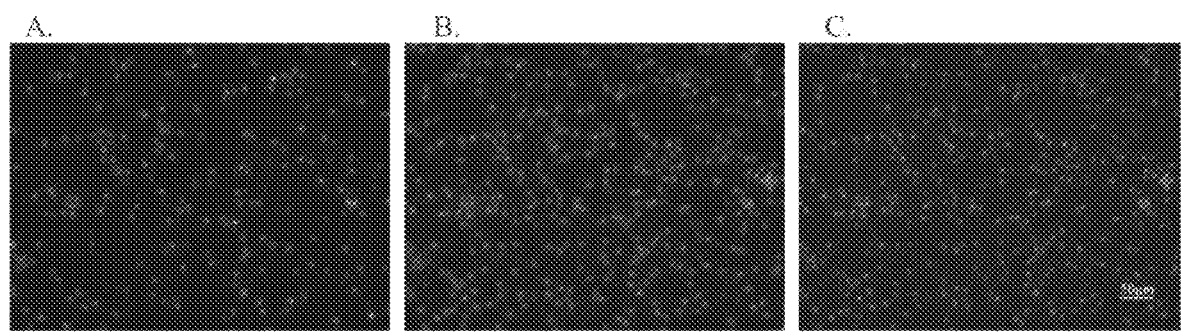
FIG. 19 shows in vivo fluorescent labeled image obtained by staining macrophages in a mouse abdominal cavity with d-KV27 fluorescent probe. Wherein the mouse peritoneal macrophages were first labeled with d-KV27 fluorescent probes in vivo, and then removed from mouse peritoneal cavity for Nucblue staining.
Figure 20:
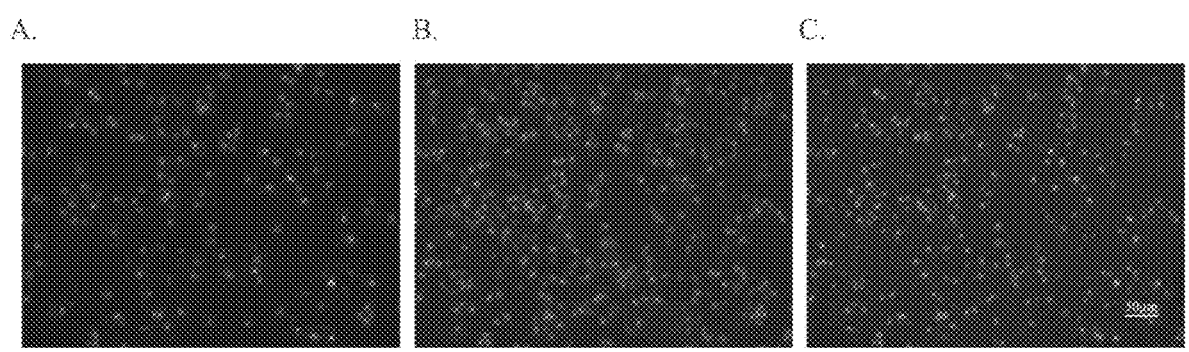
FIG. 20 shows in vivo fluorescent labeled image obtained by staining macrophages in a mouse abdominal cavity withe b-KA27 fluorescent probe. Wherein the mouse peritoneal macrophages were first labeled with b-KA27 fluorescent probes in vivo, and then removed from mouse peritoneal cavity for Nucblue staining.
Figure 21:
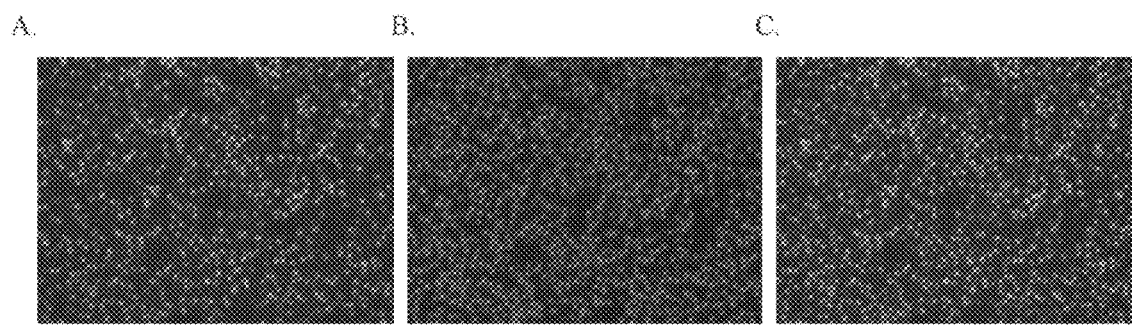
FIG. 21 shows in vivo fluorescent labeled image of macrophages in a mouse abdominal cavity using the KESG24 fluorescent probe. Wherein the mouse peritoneal macrophages were first labeled with the KESG24 fluorescent probe in vivo, and then removed from mouse peritoneal cavity for Nucblue staining.
Figure 22:
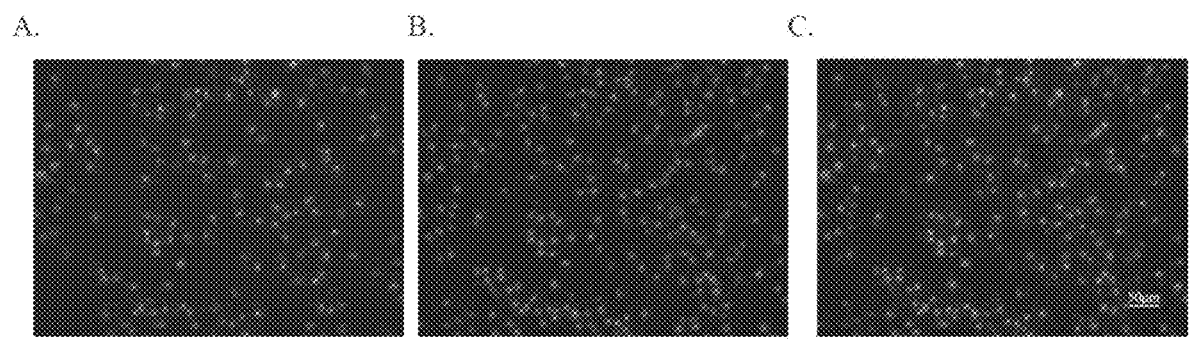
FIG. 22 shows in vivo fluorescent labeled image obtained by staining macrophages in a mouse abdominal cavity with Cx-LK24 fluorescent probe. Wherein the mouse peritoneal macrophages were first labeled with Cx-LK24 fluorescent probes in vivo, and then removed from mouse peritoneal cavity for Nucblue staining.
Figure 25:
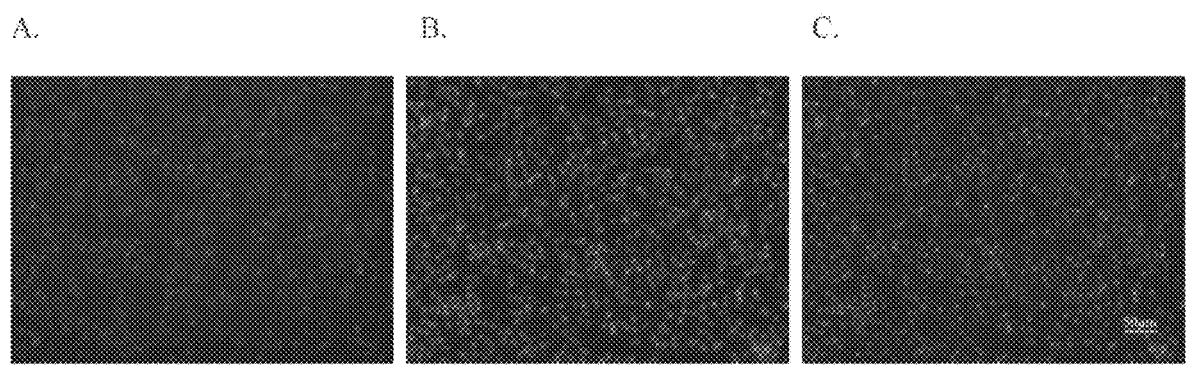
FIG. 25 shows in vivo fluorescent labeled image obtained by staining macrophages in a mouse abdominal cavity with the Hx-AVGK9 fluorescent probe. The mouse peritoneal macrophages were first labeled with the Hx-AVGK9 fluorescent probe in vivo, and then removed from mouse peritoneal cavity for Nucblue staining.
Figure 26:
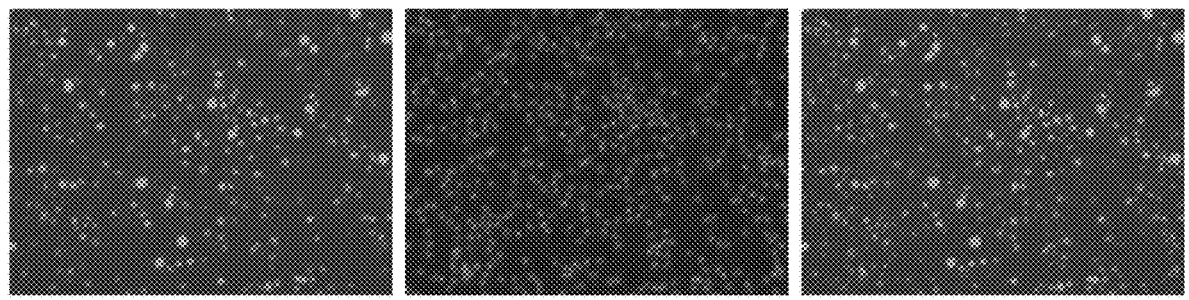
FIG. 26 shows in vivo fluorescent labeled image obtained by staining macrophages in a mouse abdominal cavity with the IK12 fluorescent probe. Wherein the mouse peritoneal macrophages were first labeled with the IK12 fluorescent probe in vivo, and then removed from mouse peritoneal cavity for Nucblue staining.
Figure 27:
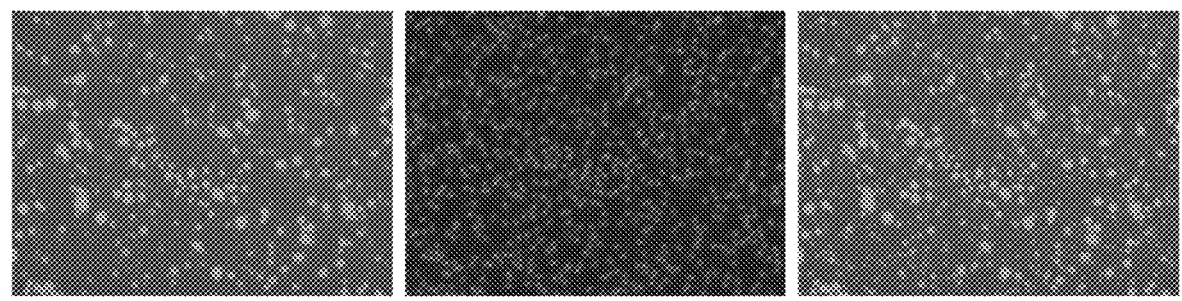
FIG. 27 shows in vivo fluorescent labeled image obtained by staining macrophages in a mouse abdominal cavity with Hx-VVGK12 fluorescent probe. Wherein the mouse peritoneal macrophages were first labeled with the Hx-VVGK12 fluorescent probe in vivo, and then removed from mouse peritoneal cavity for Nucblue staining.

| Species | Sequences | In vivo targeted imaging effect | Figures | Names |
|---|---|---|---|---|
| Human (Homo sapiens) | AILEVLQS-Y (SEQ ID NO.: 1) | + | FIG. 2 | AK9 |
| Human (Homo sapiens) | LRAILEVLQS-Y (SEQ ID NO.: 2) | +++ | FIG. 3 | LK11 |
| Human (Homo sapiens) | ILRAILEVLQS-Y (SEQ ID NO.: 3) | +++ | FIG. 26 | IK12 |
| Human (Homo sapiens) | AAILRAILEVLQS-Y (SEQ ID NO.: 4) | ++++ | FIG. 4 | AK14 |
| Rhesus monkey (Macaca mulatto) | EQPDPGAVAAAAILRAILEVLQS-Y (SEQ ID NO.: 16) | +++ | FIG. 5-12 | EK24 |
| Human (Homo sapiens) | EQPDPGAVAAAAILRAILEVLQS-Y (SEQ ID NO.: 5) | +++ | FIG. 5-12 | EK24 |
| Human (Homo sapiens) | X-EQPDPGAVAAAAILRAILEVLQS (SEQ ID NO.: 5) | +++ | FIG. 13-14 | KS24 |
| Human (Homo sapiens) | PGAVAAAAILRAILEVLQS-Y (SEQ ID NO.: 6) | ++++ | FIG. 15 | PK20 |
| Human (Homo sapiens) | X-TKNMEAGAGRASYISSARLEQPDPGAVAAAAILRAILEVLQS (SEQ ID NO.: 7) | ++ | FIG. 16 | TS42 |
| Chickens (Gallus gallus) | LQPDPGAVAAAAVLRAVLEGLQG-Y (SEQ ID NO.: 12) | + | FIG. 17 | LK24 |
| Rat (Rattus norvegicus) | X-DQPDPGAVAAAAIFRAILEVLQTKAA (SEQ ID NO.: 13) | +++ | FIG. 18 | r-KA27 |
| Dog (Canis lupus) | X-DQPDPGAVAAAAILRTILEVLQSQGV (SEQ ID NO.: 14) | ++ | FIG. 19 | d-KV27 |
| Pig (Sus scrofa) | X-DQPDPGAVAAAAILRAILEVLQSQGA (SEQ ID NO.: 15) | +++ | FIG. 20 | b-KA27 |
| Cow (Bos Taurus) | X-DQPDPGAVAAAAILRAILEVLQSQGA (SEQ ID NO.: 18) | +++ | FIG. 20 | b-KA27 |
| Modified sequence | AVLEVLQG-Y (SEQ ID NO.: 8) | + | FIG. 25 | Hx-AVGK9 |
| Modified sequence | VLRAVLEVLQG-Y (SEQ ID NO.: 9) | ++++ | FIG. 27 | Hx-VVGK12 |
| Modified sequence | X-EQPDPSAVAAAAILRAILEVLQG (SEQ ID NO.: 10) | +++ | FIG. 21 | KESG24 |
| Modified sequence | LQPDPSAVAAAAVLRAVLEVLQG-Y (SEQ ID NO.: 11) | +++ | FIG. 22 | Cx-LK24 |

X, Y = reporter or cysteine/lysine + reporter (rhodamine or FITC)

From the results in Table 1, it can be seen that all the polypeptides from the C-terminal fragments of Triokinase/FMN cyclases of different animal species or modified sequences thereof can specifically target monocytes/macrophages. Specifically, AK9, LK11, IK12, AK14, PK20, EK24, KS24, TS42 derived from human Triokinase/FMN cyclase, LK24 derived from chicken Triokinase/FMN cyclase, r-KA27 derived from rat Triokinase/FMN cyclase, d-KV27 derived from dog Triokinase/FMN cyclase, b-KA27 derived from pig and cattle Triokinase/FMN cyclase and EK24 derived from rhesus monkey Triokinase/FMN cyclase as well as the modified sequences can effectively recognize macrophages in vivo. It indicates that highly conserved polypeptide fragments from the C-terminal fragments of Triokinases/FMN cyclases of different species can be used as probes to label monocytes/macrophages. The following examples provide further relevant experimental results.

Example 5. Fluorescent Labeling of Macrophages in a Mouse Abdominal Cavity by the LK11 Fluorescent Probe Referring to Example 3, using the same treatment method, the mouse peritoneal macrophages were first labeled in vivo using the LK11 fluorescent probe, and then removed from the mouse abdominal cavity for nuclear fluorescence labeling with Nucblue. The resulted macrophages were observed under a fluorescence microscope (20×, light source 50%, exposure 200 ms, gain 5). The results are shown in FIG. 3.

FIG. 3A is a labeled image obtained by using the LK11 fluorescent probe (shown in red fluorescence in the original fluorescence color image), and FIG. 3B is a nuclear-staining image obtained by using Nucblue (shown in blue fluorescence in the original fluorescence color image), and FIG. 3C is a merged image of FIGS. 3A and 3B.

It can be seen from FIG. 3 that the macrophages extracted from the mouse abdominal cavity can be labeled with the LK11 fluorescent probe.

Example 6. Fluorescent Labeling of Macrophages in a Mouse Abdominal Cavity by the AK14 Fluorescent Probe Referring to Example 3, using the same treatment method, the mouse peritoneal macrophages were first labeled in vivo using the AK14 fluorescent probe, and then removed from the mouse abdominal cavity for Nuclear fluorescence labeling with Nucblue. The macrophages were observed under a fluorescence microscope (20×, light source 10%, exposure 200 ms, gain 5). The results are shown in FIG. 4.

FIG. 4A is a labeled image obtained by using the AK14 fluorescent probe (shown in red fluorescence in the original fluorescence color image), and FIG. 4B is a nuclear-staining image obtained by using Nucblue (shown in blue fluorescence in the original fluorescence color image), and FIG. 4C is a merged image of FIGS. 4A and 4B.

It can be seen from FIG. 4 that the macrophages extracted from the mouse abdominal cavity can be labeled with the AK14 fluorescent probe.

Example 7. In Vitro Fluorescence Labeled Staining of a Mouse Macrophage Cell Line by the EK24 Probe Culture the mouse macrophage cell line RAW264.7 in a 96-well plate, wash the wells once with 1×PBS buffer or a serum-free DMEM incomplete medium, remove the washing liquid, add EK24 solution of 10 μM which had been diluted with 100 μL of serum-free DMEM incomplete medium, and incubate in a cell culture incubator for 1 h. After that, wash the wells twice with 1× PBS buffer or the serum-free DMEM incomplete medium. Then, add DMEM complete medium containing 10% FBS and 1% streptomycin-penicillin, and double-stain the cells using nuclear dye Nucblue and observe under EVOS® FL Auto fluorescence microscope (Life Technologies, light source 10%, exposure 200 ms, gain 5). The results are shown in FIG. 5.

Figure 5:
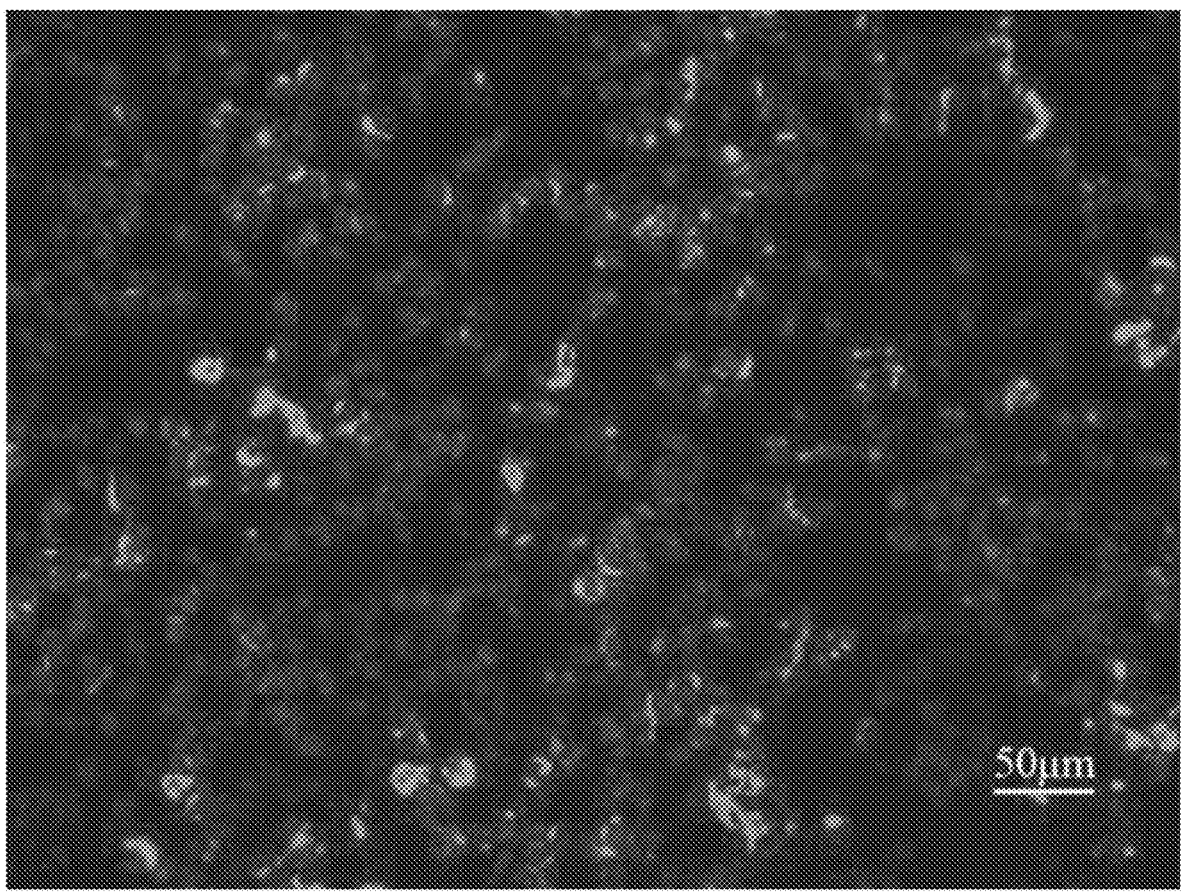
FIG. 5 shows an in vitro fluorescent labeled image obtained by staining mouse macrophage cell line RAW264.7 with EK24 probe. The macrophage cell line RAW264.7 was stained with the EK24 probe (shown in red in the original fluorescence color image) and Nucblue (shown in blue in the original fluorescence color image).

FIG. 5 shows images of in vitro cultured mouse macrophage cell line that were fluorescent labeled using the EK24 fluorescent probe (shown in red fluorescence in the original fluorescence color image) and Nucblue (shown in blue in the original fluorescence color image).

It can be seen from FIG. 5 that the macrophage cell line RAW264.7 can be labeled with the EK24 fluorescent probe (shown in red fluorescence in the original fluorescence color image).

Example 8. In Vivo Fluorescent Labeling of Macrophages in a Mouse Abdominal Cavity by the EK24 Fluorescent Probe Referring to Example 3, using the same processing method, the mouse peritoneal macrophages were first labeled in vivo using the EK24 fluorescent probe, and then removed from the mouse abdominal cavity for nuclear fluorescence labeling with Nucblue. Observe the macrophages under a fluorescence microscope (20×, light source 10%, exposure 200 ms, gain 5). The results are shown in FIG. 6.

FIG. 6A is a fluorescent labeled image obtained by using the EK24 fluorescent probe (shown in red fluorescence in the original fluorescence color image), and FIG. 6B is a nuclear stained image obtained by using Nucblue (shown in blue fluorescence in the original fluorescence color image), and FIG. 6C is a merged image of FIGS. 6A and 6B.

Figure 6:
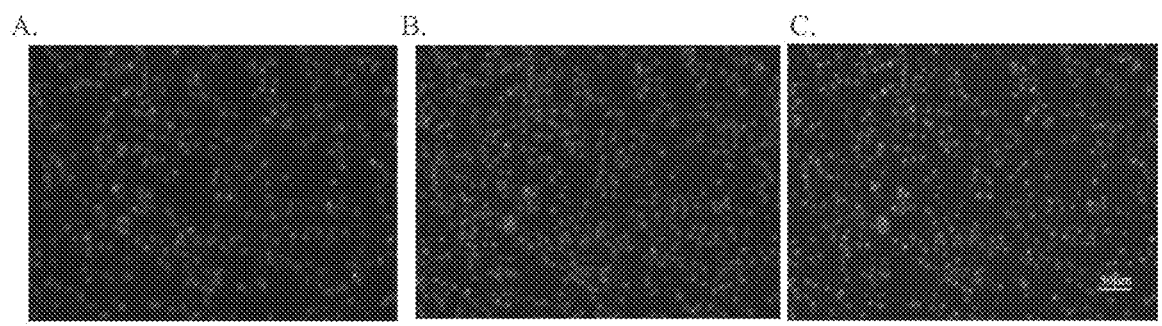
FIG. 6 shows in vivo fluorescent labeled images obtained by staining macrophages in a mouse abdominal cavity with EK24 probe. The mouse peritoneal macrophages were first labeled with the EK24 probe in vivo, and then removed from mouse peritoneal cavity for Nucblue staining.

It can be seen from FIG. 6 that the macrophages extracted from the mouse abdominal cavity can be labeled with the EK24 fluorescent probe.

Figure 7:
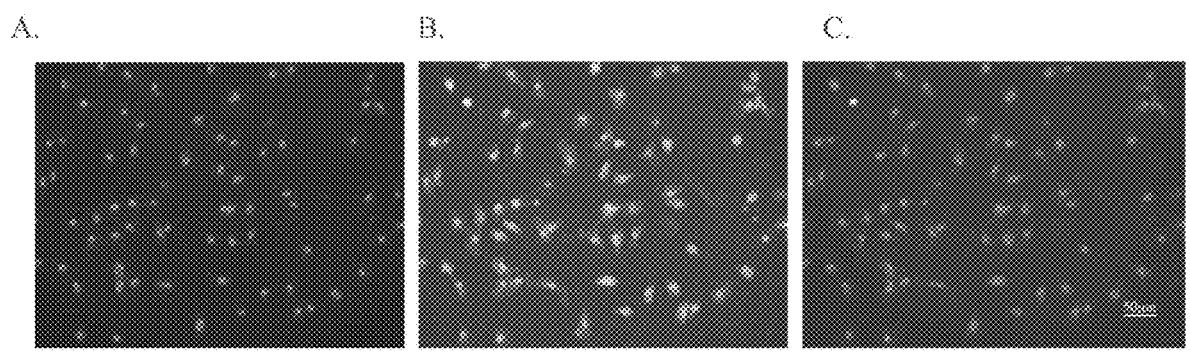
FIG. 7 shows fluorescent labeled images obtained by staining macrophages, which were removed from the mouse abdominal cavity and cultured in vitro, with EK24 probe.

Example 9. In Vitro Fluorescent Labeling of Cultured Macrophages Isolated from Mouse Peritoneal Cavity by EK24 Probe Inject 5 mL of serum-free DMEM incomplete medium into the abdominal cavity of 5 to 8 weeks old mice, massage the abdominal cavity gently for 10 min, and sacrifice the mice by cervical vertebra dislocation. Extract the fluid from the abdominal cavity gently with a syringe, inject into a 5 mL centrifuge tube and centrifuge at 1000 rpm for 5 min, remove the supernatant, and resuspend the collected ex-vivo cells in DMEM/F12 medium containing 10% FBS, then add into a 96-well plate for culture. Generally, if cells are taken intraperitoneally for in vitro culture, macrophages would tend to adhere to the bottom of the well, and other cells would be washed off. The cells were cultured for more than 2 days until the cells attached to the bottom firmly. At this time, the cells remaining in the wells were basically macrophages. Select two wells, one as a control and the other as an experimental well. The cells of the control were nuclear stained with Nucblue. The experimental well was added with a premix of AlexaFluor®488 anti-mouse F4/80 antibody (Biolegend) and EK24 fluorescent probe, and then incubated for 1 h at 37° ° C. The premix contained 10 μM of EK24 solution and 2 μL of Alexa Fluor®488 anti-mouse F4/80 antibody diluted with 100 μL of serum-free DMEM incomplete medium. The remaining treatment steps can refer to the above Example 3. The cells were observed under a fluorescence microscope (20× objective lens, light source 10%, exposure 200 ms, gain 5). The results are shown in FIG. 7.

FIG. 7A shows a fluorescent labeled image obtained by using the EK24 fluorescent probe (shown in red fluorescence in the original fluorescence color image) and nuclear stained image obtained by using Nucblue (shown in blue fluorescence in the original fluorescence color image).

FIG. 7B shows a fluorescent labeled image obtained by using the F4/80 antibody (shown in green fluorescence in the original fluorescence color image) and nuclear stained image obtained by using Nucblue (shown in blue fluorescence in the original fluorescence color image). It can be seen from FIG. 7B that almost all the cells obtained by intraperitoneal massage were labeled with F4/80 antibody, indicating that these labeled cells were macrophages.

FIG. 7C is a merged image of FIGS. 7A, and 7B. From this figure, it can be seen that both the EK24 fluorescent probe label and the F4/80 antibody label are co-localized on the same cells. This result indicates that cells labeled with the F4/80 antibody are also labeled with the EK24 fluorescent probe, which further indicates that the EK24 fluorescent probe can target and recognize macrophages.

Example 10. In Vitro Fluorescent Labeling of Primary Macrophages from Rat Peritoneal Cavity by EK24 Fluorescent Probe With the same process as in Example 9, extract cells from the abdominal cavity of 5 to 8 weeks old SD rats using 20 mL serum-free DMEM incomplete medium and culture the cells in a 96-well plate. After culturing for more than 2 days until the cells attached to the bottom firmly, a well was selected and added with EK24 fluorescent probe for incubation. Then the cells were observed under a fluorescence microscope (20×, light source 10%, exposure 200 ms, gain 5). The results are shown in FIG. 8.

FIG. 8A shows images obtained from direct fluorescent labeling of macrophages from a rat abdominal cavity with the EK24 fluorescent probe (shown in red fluorescence in the original fluorescence color image) and Nucblue (shown in blue fluorescence in the original fluorescence color image). FIG. 8B shows images obtained by fluorescent labeling of primary macrophages, which were taken from rat peritoneal cavity and cultured for more than 2 days in vitro, with the EK24 fluorescent probe (shown in red fluorescence in the original fluorescence color image) and Nucblue (shown in blue fluorescence in the original fluorescence color image).

Figure 8:
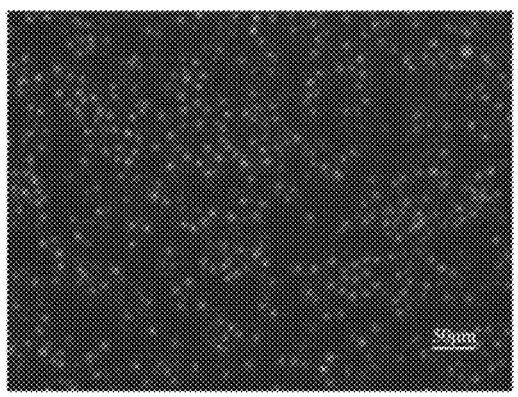
FIG. 8 shows fluorescent labeled images obtained by staining macrophages from rat peritoneal cavity with EK24 fluorescent probe.
Figure 8:
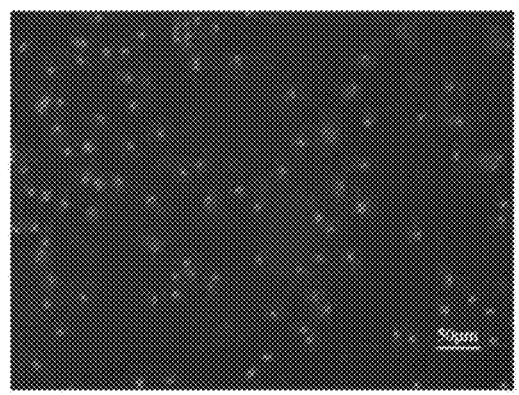

It can be seen from FIG. 8 that the EK24 fluorescent probe can effectively label the in vitro cultured primary macrophages from rat peritoneal cavity.

Example 11. In Vitro Fluorescence Labeling of Mouse Primary Monocyte Precursors By EK24 Probe As described above, macrophages were derived from monocytes in blood, and monocytes were transformed from monocyte precursors in bone marrow: In order to verify whether the EK24 fluorescent probe can recognize monocyte precursors, the EK24 fluorescent probe and Nucblue were used to label monocytes from the mesenchyme of bone marrow:

In a bio-safety hood, take the femur of a Kunming mouse, cut off both ends of the femur, wash medulla out with PBS, and collect cells by centrifugation. The collected ex-vivo cells were resuspended in F12/DMEM medium containing 10% FBS and 1% streptomycin-penicillin, and add to a 96-well plate for culture. After culturing for more than 2 days until the cells attached to the bottom firmly, the cells remaining in the wells were basically monocyte precursors. Treat with reference to Example 9. Then the cells were observed under a fluorescence microscope (200×, light source 50%, exposure 200 ms, gain 5). The results are shown in FIG. 9.

Figure 9:
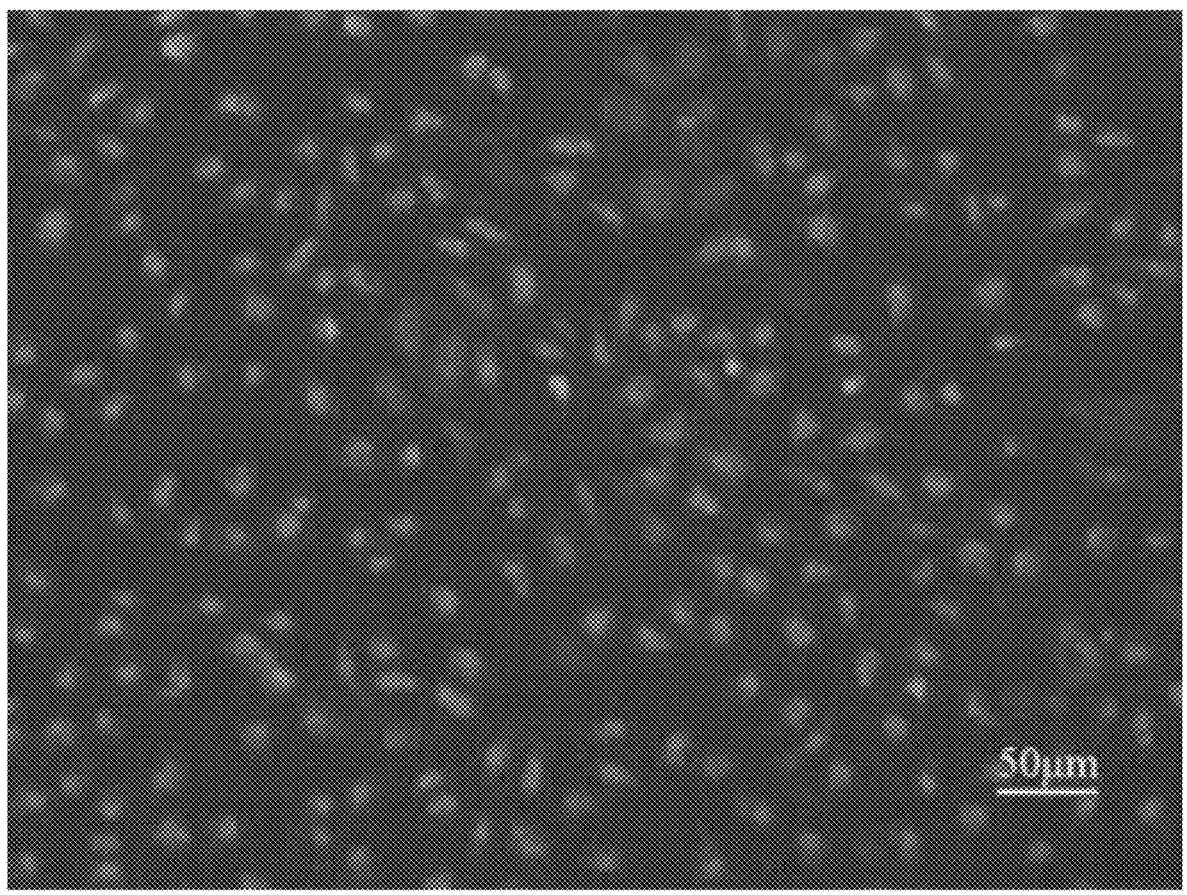
FIG. 9 shows a fluorescent labeled image obtained by staining cultured monocyte precursors isolated from mouse bone marrow; with EK24 fluorescent probe (shown in red in the original fluorescence color image) and Nucblue (shown in blue in the original fluorescence color image).

FIG. 9 shows images obtained with direct fluorescent labeling of monocyte precursors from the mesenchyme of mouse bone marrow with the EK24 fluorescent probe (shown in red fluorescence in the original fluorescence color image) and Nucblue (shown in blue fluorescence in the original fluorescence color image). It can be seen that the EK24 fluorescent probe (shown in red fluorescence in the original fluorescence color image) is capable of labeling monocyte precursors from the mesenchyme of mouse bone marrow:

Example 12. In Vitro Fluorescent Labeling of Rat Primary Monocyte Precursors by the EK24 Fluorescent Probe With a similar process to Example 11, mononuclear cell precursors from rat femoral bone marrow were taken and cultured, and then labeled by using EK24 fluorescent probe and Nucblue. Then the cells were observed under a fluorescence microscope (20×, light source 10%, exposure 200 ms, gain 5). The results are shown in FIG. 10.

Figure 10:
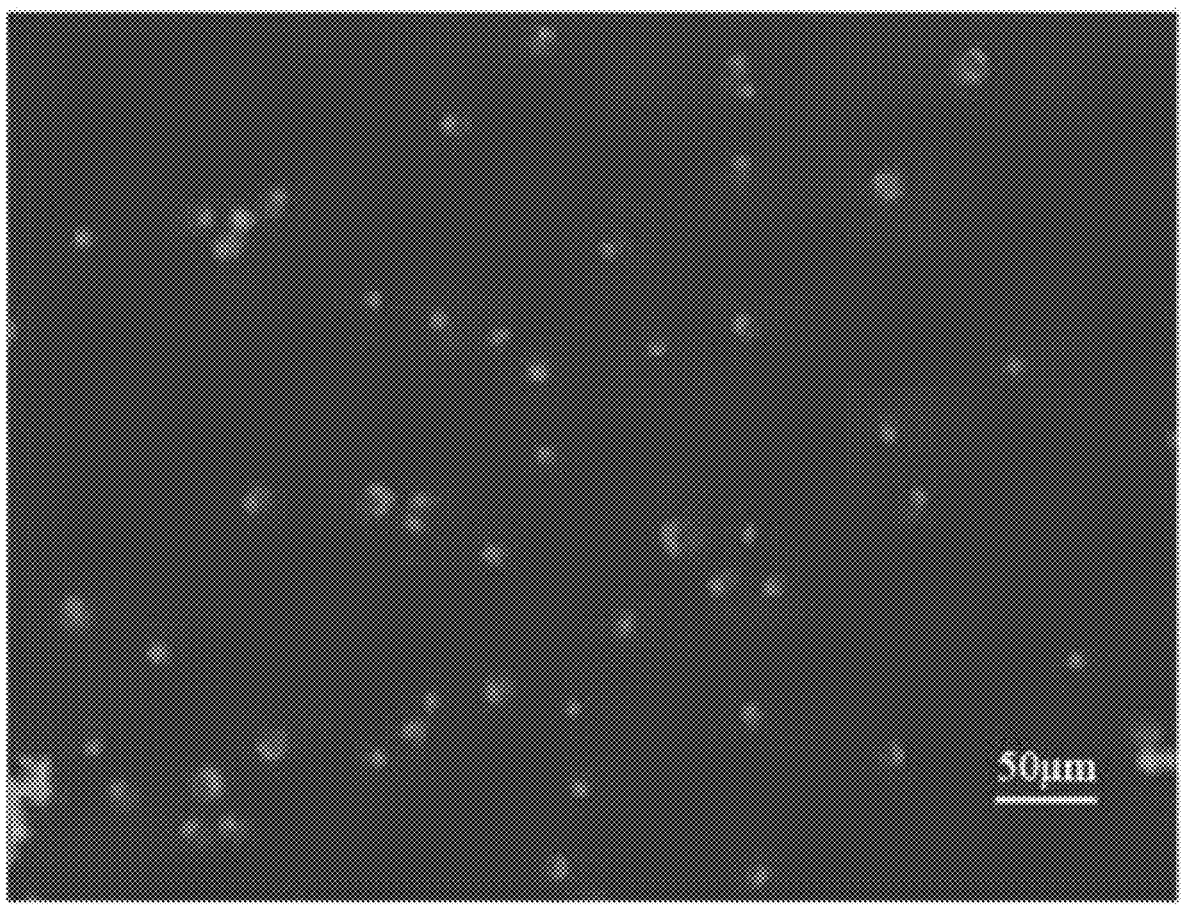
FIG. 10 shows a fluorescent labeled image obtained by staining cultured monocyte precursors isolated from rat bone marrow; with EK24 fluorescent probe (shown in red in the original fluorescence color image) and Nucblue (shown in blue in the original fluorescence color image).

FIG. 10 shows images obtained by fluorescent labeling of monocyte precursors from rat bone marrow mesenchyme with the EK24 fluorescent probe (shown in red fluorescence in the original fluorescence color image) and Nucblue (shown in blue fluorescence in the original fluorescence color image). It can be seen that the EK24 fluorescent probe (shown in red fluorescence in the original fluorescence color image) is also capable of labeling monocyte precursors from mesenchyme of rat bone marrow:

Example 13. In Vitro Fluorescent Labeling of Primary Monocyte Precursors of New Zealand White Rabbit by the EK24 Fluorescent Probe With a similar process to Example 11, bone marrow monocyte precursors of New Zealand White Rabbit were taken and cultured, then labeled by using EK24 fluorescent probe and Nucblue. Then the cells were observed under a fluorescence microscope (20×, light source 10%, exposure 200 ms, gain 5). The results are shown in FIG. 11.

FIG. 11 shows images obtained from directly fluorescent labeling of monocyte precursors from mesenchyme of New Zealand White Rabbit bone marrow with the EK24 fluorescent probe (shown in red fluorescence in the original fluorescence color image) and Nucblue (shown in blue fluorescence in the original fluorescence color image). It can be seen that the EK24 fluorescent probe (shown in red fluorescence in the original fluorescence color image) is also capable of labeling monocyte precursors from New Zealand White Rabbit bone marrow mesenchyme.

Example 14. EK24 Fluorescent Probe Selective Labeling and Staining of Cultured Peritoneal Macrophages Among Other Cells Released from Enzyme-Digested Mesenterium Take 5 to 8-week-old Kunming mice, inject intraperitoneally with 5 mL of serum-free DMEM incomplete medium. After 1 hour, sacrifice the mice by cervical vertebra dislocation. Make an incision on the skin of abdominal cavity, pierce the abdominal wall muscle using the syringe, and extract the fluid in the abdominal cavity of the mice. Wash twice with 1×PBS, collect peritoneal cells by centrifugation. Also take the mesenteries of the Kunming mice and purge twice with 1×PBS in centrifuge tubes. Incubate the obtained peritoneal cells and mesenteries in 0.25% trypsin solution and digest for 30 minutes. Enrich the cells by centrifugation, and then culture for 3 days in a 96-well plate using F12/DMEM culture solution containing 10% FBS and 1% streptomycin-penicillin. Referring to Example 5, label with the EK24 fluorescent probe and Nucblue. Then the cells were observed under a fluorescence microscope (20×, light source 10%, exposure 200 ms, gain 5). The results are shown in FIG. 12.

FIG. 12A is an image obtained by labeling with the EK24 fluorescent probe (shown in red fluorescence in the original fluorescence color image), and FIG. 12B is an image obtained by nuclear staining with Nucblue (shown in blue fluorescence in the original fluorescence color image), and FIG. 12C is a merged image of FIGS. 12A and 12B. It can be seen from the figures that the EK24 fluorescent probe only stains macrophages (as shown by the solid arrow in FIG. 12C, cells labeled with both blue and red fluorescences), and not stain non-macrophages (as shown by the hollow arrow in FIG. 12C, cells labeled with only blue fluorescence without red fluorescence).

Example 15. In Vivo Fluorescent Labeling of Macrophages in a Mouse Abdominal Cavity by the KS24 Fluorescent Probe Referring to Example 3, using the same treatment process, the mouse peritoneal macrophages were first labeled in vivo using the KS24 fluorescent probe, and then removed from the mouse abdominal cavity for Nuclear fluorescence labeling with Nucblue. Then the labeled macrophages were observed under a fluorescence microscope (20×, light source 10%, exposure 200 ms, gain 5). The results are shown in FIG. 13.

FIG. 13A is an image obtained by labeling with the KS24 fluorescent probe (shown in red fluorescence in the original fluorescence color image), and FIG. 13B is an image obtained by nuclear staining with Nucblue (shown in blue fluorescence in the original fluorescence color image), and FIG. 13C is a merged image of FIGS. 13A and 13B.

It can be seen from FIG. 13 that the macrophages extracted from the mouse abdominal cavity can be labeled with the KS24 fluorescent probe.

Example 16. In Vitro Fluorescent Labeling of Mouse Peritoneal Macrophages by the EK24 Fluorescent Probe at Different Incubation Times Referring to Example 9, using the same treatment process, the macrophages from mouse abdominal cavity were obtained. After culturing for 6 days, the cultured peritoneal cells were labeled with KS24 fluorescent probes for different incubation times. Then the cells were observed under a fluorescence microscope (20×, light source 20%, exposure 200 ms, gain 5). The results are shown in FIG. 14.

FIG. 14A shows the fluorescent label results obtained by incubating with the KS24 fluorescent probe for 10 min. FIG. 14B shows the fluorescent label results obtained by incubating with the KS24 fluorescent probe for 20 min. FIG. 14C shows the fluorescent label results obtained by incubating with the KS24 fluorescent probe for 40 min. FIG. 14D shows the fluorescent label results obtained by incubating with the KS24 fluorescent probe for 80 min. Nucblue (blue fluorescence) was further used for nuclear staining. In each of FIGS. 14A, 14B, 14C, and 14D, i) is an image labeled with the KS24 fluorescent probe (shown in red fluorescence in the original fluorescence color image), and ii) is an image obtained by nuclear staining with Nucblue (shown in blue fluorescence in the original fluorescence color image), and iii) is a merged image of i) and ii).

It can be seen from FIG. 14 that the KS24-labeled fluorescence of the cells gradually becomes stronger with the incubation time. The fluorescence can be even detected with microscope when incubating only for 10 min. It is sufficient to show that KS24 fluorescent probe can quickly and efficiently label mouse peritoneal macrophages.

Example 17. In Vivo Fluorescent Labeling of Macrophages in a Mouse Abdominal Cavity by the PK20 Fluorescent Probe Referring to Example 3, using the same treatment method, the mouse peritoneal macrophages were first labeled in vivo using the PK20 fluorescent probe, and then removed from the mouse abdominal cavity for Nuclear fluorescent labeling with Nucblue. Then the macrophages were observed under a fluorescence microscope (20×, light source 10%, exposure 200 ms, gain 5), and the results are shown in FIG. 15.

FIG. 15A is an image obtained from fluorescent labeling using PK20 fluorescent probe (shown in red fluorescence in the original fluorescence color image), and FIG. 15B is an image obtained by nuclear staining with Nucblue (shown in blue fluorescence in the original fluorescence color image), and FIG. 15C is a merged image of FIGS. 15A and 15B.

It can be seen from FIG. 15 that the macrophages extracted from the mouse abdominal cavity can be labeled with the PK20 fluorescent probe.

Example 18. In Vivo Fluorescent Labeling of Macrophages in a Mouse Abdominal Cavity by the TS42 Fluorescent Probe Referring to Example 3, using the same treatment process, the mouse peritoneal macrophages were first labeled in vivo using the TS42 fluorescent probe (carrying the FITC group), and then removed from the mouse abdominal cavity for nuclear fluorescence labeling with Nucblue. Then the macrophages were observed under a fluorescence microscope (20×, light source 50%, exposure 200 ms, gain 5). The results are shown in FIG. 16.

FIG. 16A is an image by labeling with the TS42 fluorescent probe (shown in green fluorescence in the original fluorescence color image), and FIG. 16B is an image by nuclear staining with Nucblue (shown in blue fluorescence in the original fluorescence color image), and FIG. 16C is a merged image of FIGS. 16A and 16B.

It can be seen from FIG. 16 that the macrophages extracted from the mouse abdominal cavity can be labeled with the TS42 fluorescent probe.

Example 19. In Vivo Fluorescent Labeling of Macrophages in a Mouse Abdominal Cavity by the LK24 Fluorescent Probe Referring to Example 3, using the same treatment process, the mouse peritoneal macrophages were first labeled in vivo using the LK24 fluorescent probe, and then removed from the mouse abdominal cavity for nuclear fluorescence labeling with Nucblue. Then the macrophages were observed under a fluorescence microscope (20×). The results are shown in FIG. 17.

FIG. 17 shows the images observed under a fluorescence microscope (light source 50%, exposure 200 ms, gain 5). FIG. 17A is an image obtained by labeling with the LK24 fluorescent probe (shown in red fluorescence in the original fluorescence color image), and FIG. 17B is an image obtained by nuclear staining with Nucblue (shown in blue fluorescence in the original fluorescence color image), and FIG. 17C is a merged image of FIGS. 17A and 17B.

It can be seen from FIG. 17 that the macrophages extracted from the mouse abdominal cavity can also be labeled with the LK24 fluorescent probe.

Example 20. In Vivo Fluorescent Labeling of Macrophages in a Mouse Abdominal Cavity by the r-KA27 Fluorescent Probe Referring to Example 3, using the same treatment process, the mouse peritoneal macrophages were first labeled in vivo using the r-KA27 fluorescent probe, and then removed from the mouse abdominal cavity for Nuclear fluorescence labeling with Nucblue. Then the macrophages were observed under a fluorescence microscope (20×, light source 10%, exposure 200 ms, gain 5). The results are shown in FIG. 18.

FIG. 18A is an image obtained by labeling with the KA27 fluorescent probe (shown in red fluorescence in the original fluorescence color image), and FIG. 18B is an image obtained by nuclear staining with Nucblue (shown in blue fluorescence in the original fluorescence color image), and FIG. 18C is a merged image of FIGS. 18A and 18B.

It can be seen from FIG. 18 that the macrophages extracted from the mouse abdominal cavity can be labeled with the r-KA27 fluorescent probe.

Example 21. In Vivo Fluorescent Labeling of Macrophages in a Mouse Abdominal Cavity by the d-KV27 Fluorescent Probe Referring to Example 3, using the same treatment process, the mouse peritoneal macrophages were first labeled in vivo using the d-KV27 fluorescent probe, and then removed from the mouse abdominal cavity for nuclear fluorescence labeling with Nucblue. Then the macrophages were observed under a fluorescence microscope (20×, light source 10%, exposure 200 ms, gain 5). The results are shown in FIG. 19.

FIG. 19A is an image obtained by labeling with the d-KV27 fluorescent probe (shown in red fluorescence in the original fluorescence color image), and FIG. 19B is an image obtained by nuclear staining with Nucblue (shown in blue fluorescence in the original fluorescence color image), and FIG. 19C is a merged image of FIGS. 19A and 19B.

It can be seen from FIG. 19 that the macrophages extracted from the mouse abdominal cavity can be labeled with the d-KV27 fluorescent probe.

Example 22. In Vivo Fluorescent Labeling of Macrophages in a Mouse Abdominal Cavity by the b-KA27 Fluorescent Probe Referring to Example 3, using the same treatment process, the mouse peritoneal macrophages were first labeled in vivo using the b-KA27 fluorescent probe, and then removed from the mouse abdominal cavity for nuclear fluorescence labeling with Nucblue. Then the macrophages were observed under a fluorescence microscope (20×, light source 10%, exposure 200 ms, gain 5). The results are shown in FIG. 20.

FIG. 20A is an image by labeling with the b-KA27 fluorescent probe (shown in red fluorescence in the original fluorescence color image), and FIG. 20B is an image obtained by nuclear staining with Nucblue (shown in blue fluorescence in the original fluorescence color image), and FIG. 20C is a merged image of FIGS. 20A and 20B.

It can be seen from FIG. 20 that the macrophages extracted from the mouse abdominal cavity can be labeled with the b-KA27 fluorescent probe.

Example 23. In Vivo Fluorescent Labeling of Macrophages in a Mouse Abdominal Cavity by the KESG24 Fluorescent Probe Referring to Example 3, using the same treatment process, the mouse peritoneal macrophages were first labeled in vivo using the KESG24 fluorescent probe, and then removed from the mouse abdominal cavity for nuclear fluorescence labeling with Nucblue. Then the macrophages were observed under a fluorescence microscope (20×, light source 50%, exposure 200 ms, gain 5). The results are shown in FIG. 21.

FIG. 21A is an image obtained by labeling with the KESG244 fluorescent probe (shown in red fluorescence in the original fluorescence color image), and FIG. 21B is an image obtained by nuclear staining with Nucblue (shown in blue fluorescence in the original fluorescence color image), and FIG. 21C is a merged image of FIGS. 21A and 21B.

It can be seen from FIG. 21 that the macrophages extracted from the mouse abdominal cavity can be labeled with the KESG24 fluorescent probe.

Example 24. In Vivo Fluorescent Labeling of Macrophages in a Mouse Abdominal Cavity by the Cx-LK24 Fluorescent Probe Referring to Example 3, using the same treatment process, the mouse peritoneal macrophages were first labeled in vivo using the Cx-LK24 fluorescent probe, and then removed from the mouse abdominal cavity for nuclear fluorescence labeling with Nucblue. Then the macrophages were observed under a fluorescence microscope (20×, light source 50%, exposure 200 ms, gain 5). The results are shown in FIG. 22.

FIG. 22A is an image obtained by labeling with the Cx-LK24 fluorescent probe (shown in red fluorescence in the original fluorescence color image), and FIG. 22B is an image obtained by nuclear staining with Nucblue (shown in blue fluorescence in the original fluorescence color image), and FIG. 22C is a merged image of FIGS. 22A and 22B.

It can be seen from FIG. 22 that the macrophages extracted from the mouse abdominal cavity can be labeled with the Cx-LK24 fluorescent probe.

Example 25. In Vivo Fluorescent Labeling of Macrophages on Mouse Abdominal Wall by the EK24 Fluorescent Probe and CD68 Antibody Referring to Example 3, using the same drug injection process, inject EK24, and FITC anti-mouse CD68 antibody (Biolegend) which was diluted with PBS from 2 μL to 500 μL. Remove mouse abdominal wall muscle for Nucblue double-staining and then observing under a fluorescence microscope (20×, light source 50%, exposure 200 ms, gain 5). The results are shown in FIG. 23.

FIG. 23A is an image obtained by labeling with the EK24 fluorescent probe (shown in red fluorescence in the original fluorescent color image), FIG. 23B is an CD68 antibody labeled image (shown in green fluorescence in the original fluorescent color image), FIG. 23C is an image obtained by nuclear staining with Nucblue (shown in blue fluorescence in the original fluorescent color image), and FIG. 23D is a merged image of FIGS. 23A, 23B and 23C.

Figure 23:
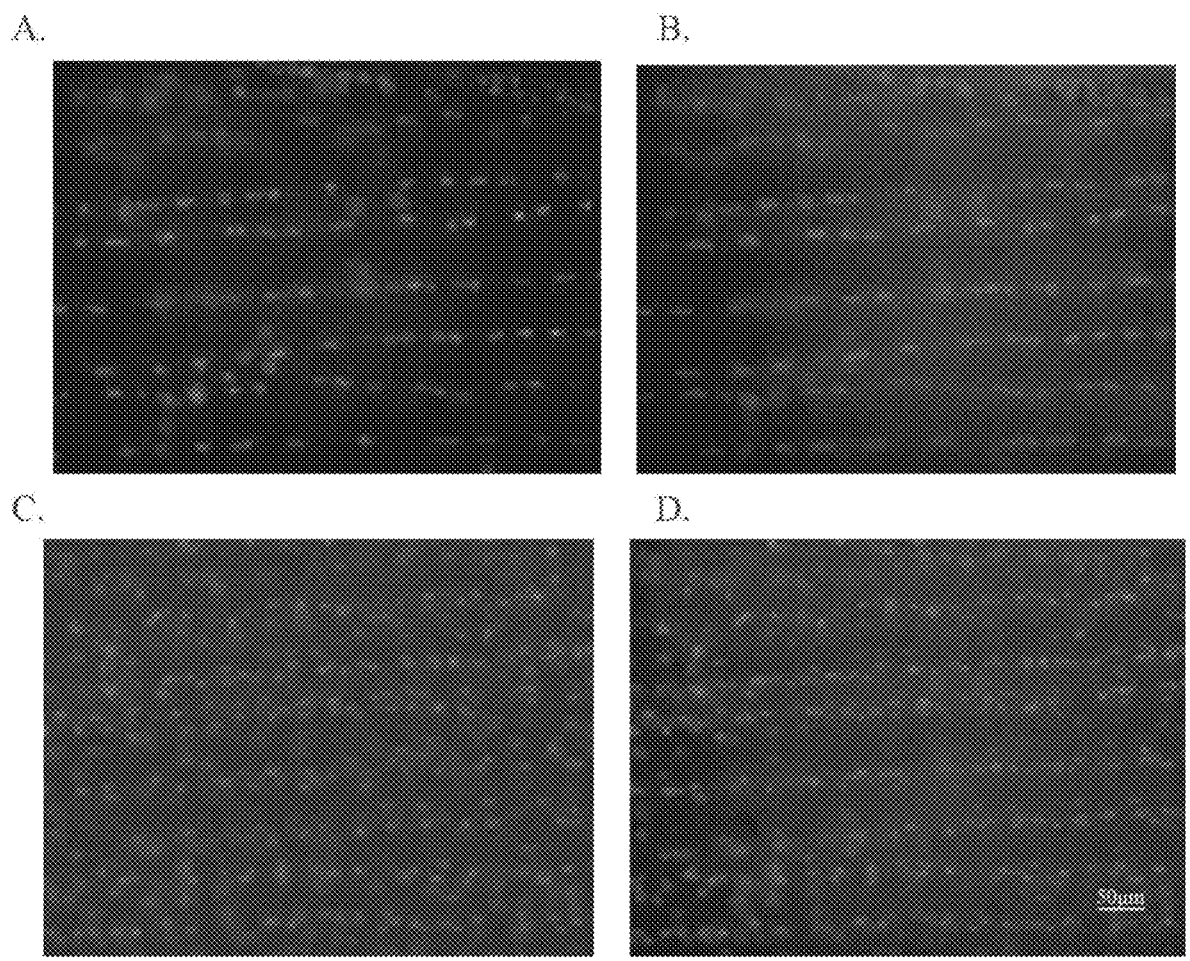
FIG. 23 shows fluorescent labeled images obtained by staining mouse abdominal wall muscle cells with the EK24 fluorescent probe and FITC anti-mouse CD68 antibody (Biolegend).

It can be seen from FIG. 23 that the macrophages on mouse abdominal wall can be labeled with the EK24 fluorescent probe, while other cells cannot be labeled.

Example 26. In Vivo Fluorescent Labeling of Mouse Pulmonary Macrophages by the EK24 Fluorescent Probe and CD11c Antibody Spray 100 µL of 50 µM EK24-drug into the lungs of 4- to 8-week-old mice through the trachea thereof, and after 18 hours, dilute 5 µL of Alexa Fluor®488 anti-mouse CD11c antibody (Biolegend) to 100 µL and then spray into the lung for 1.5 h. Dissect the mice, and take the whole lungs for observing under a fluorescence microscope (20×, light source 50%, exposure 200 ms, gain 5). The results are shown in FIG. 24.

FIG. 24A is an image obtained by labeling with the EK24 fluorescent probe (shown in red fluorescence in the original fluorescence color image), and FIG. 24B is an image obtained by labeling with CD11c antibody (shown in green fluorescence in the original fluorescence color image), and FIG. 24C is a merged image of FIGS. 24A and 24B.

Figure 24:
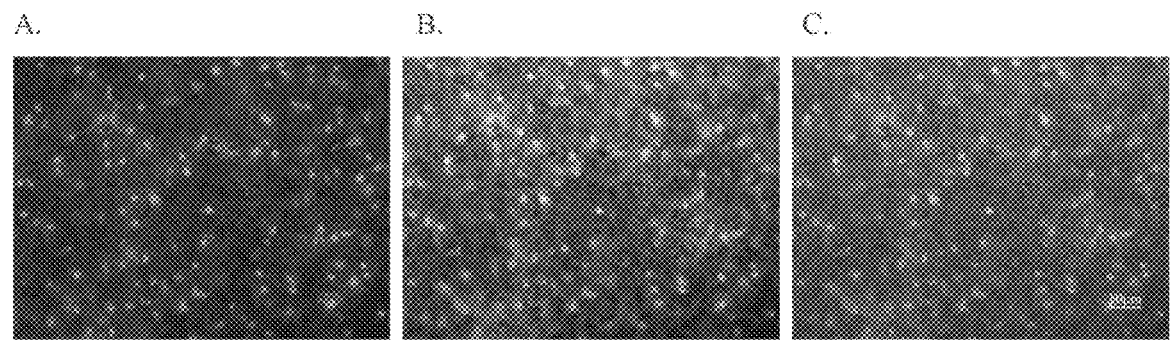
FIG. 24 shows in vivo imaging obtained by staining pulmonary macrophages with EK24 fluorescent probe and Alexa Fluor® 488 anti-mouse CD11c antibody (Biolegend) after pulmonary administration to mice.

It can be seen from FIG. 24 that both the EK24 fluorescent probe and CD11c antibody recognize the same cells in mouse alveoli, i.e. mouse alveolar macrophages.

Example 27. In Vivo Fluorescent Labeling of Macrophages in a Mouse Abdominal Cavity by the Hx-AVGK9 Fluorescent Probe Referring to Example 3, using the same treatment process, the mouse peritoneal macrophages were first labeled in vivo using the Hx-AVGK9 fluorescent probe, and then removed from the mouse abdominal cavity for nuclear fluorescence labeling with Nucblue. Then the macrophages were observed under a fluorescence microscope (20×, light source 60%, exposure 300 ms, gain 10). The results are shown in FIG. 25.

FIG. 25A is an image obtained by labeling with the Hx-AVGK9 fluorescent probe (shown in red fluorescence in the original fluorescence color image), and FIG. 25B is an image obtained by nuclear staining with Nucblue (shown in blue fluorescence in the original fluorescence color image), and FIG. 25C is a merged image of FIGS. 25A and 25B.

It can be seen from FIG. 25 that the macrophages extracted from the mouse abdominal cavity can be labeled with the Hx-AVGK9 fluorescent probe.

Example 28. In Vivo Fluorescent Labeling of Macrophages in a Mouse Abdominal Cavity by the IK12 Fluorescent Probe Referring to Example 3, using the same treatment process, the mouse peritoneal macrophages were first labeled in vivo using the IK12 fluorescent probe, and then removed from the mouse abdominal cavity for nuclear fluorescence labeling with Nucblue. Then the macrophages were observed under a fluorescence microscope (20×, light source 29%, exposure 200 ms, gain 5). The results are shown in FIG. 26.

FIG. 26A is an image obtained by labeling with the IK12 fluorescent probe (shown in red fluorescence in the original fluorescence color image), and FIG. 26B is an image obtained by nuclear staining with Nucblue (shown in blue fluorescence in the original fluorescence color image), and FIG. 26C is a merged image of FIGS. 26A and 26B.

It can be seen from FIG. 26 that the macrophages extracted from the mouse abdominal cavity can be labeled with the IK12 fluorescent probe.

Example 29. In Vivo Fluorescent Labeling of Macrophages in a Mouse Abdominal Cavity by the Hx-VVGK12 Fluorescent Probe Referring to Example 3, using the same treatment method, the mouse peritoneal macrophages were first labeled in vivo using the Hx-VVGK12 fluorescent probe, and then removed from the mouse abdominal cavity for nuclear fluorescence labeling Nucblue. Then the macrophages were observed under a fluorescence microscope (20×, light source 50%, exposure 200 ms, gain 5). The results are shown in FIG. 27.

FIG. 27A is an image obtained by labeling with the Hx-VVGK12 fluorescent probe (shown in red fluorescence in the original fluorescence color image), and FIG. 27B is an image obtaining by nuclear staining with Nucblue (shown in blue fluorescence in the original fluorescence color image), and FIG. 27C is a merged image of FIGS. 27A and 27B.

It can be seen from FIG. 27 that the macrophages extracted from the mouse abdominal cavity can be labeled with the Hx-VVGK12 fluorescent probe.

It can be concluded from the above embodiments that the probes derived from the C-terminal fragments of Triokinases/FMN cyclases of human and non-human animals can effectively recognize monocyte precursors and monocytes/macrophages.

---

We claim:

1. A polypeptide for targeting recognition of immune cells selected from the group consisting of AILEVLQS (SEQ ID NO.: 1), LRAILEVLQS (SEQ ID NO.: 2), ILRAILEVLQS (SEQ ID NO.: 3), AAILRAILEVLQS (SEQ ID NO.: 4), EQPDPGAVAAAAILRAILEVLQS (SEQ ID NO.: 5), PGAVAAAAILRAILEVLQS (SEQ ID NO.: 6) and TKNMEAGAGRASYISSARLEQPDPGAVAAAAILRAILEVLQS (SEQ ID NO.: 7).

2. The polypeptide according to claim 1, wherein the immune cells comprise lymphocytes, dendritic cells, monocyte precursors, monocytes/macrophages, basophils, eosinophils, and mastocytes.

3. The polypeptide according to claim 1, wherein the immune cells are monocyte precursors or monocytes/macrophages.

4. A composition comprising the polypeptide for targeted recognition of immune cells according to claim 1.

5. The composition according to claim 4, further comprising a reporter.

6. The composition according to claim 5, wherein the reporter group is linked to the N terminus and/or C-terminus of the polypeptide.

7. The composition according to claim 4, wherein the polypeptide is linked to the reporter through a cysteine residue or a lysine residue which is attached to the polypeptide.

8. The composition according to claim 4, wherein the reporter is a chromogenic enzyme, a fluorescent labeling group, a chemiluminescent labeling group, an isotope, or a magnetic functional group.

9. The composition according to claim 5, wherein the composition is used for in vivo labeling and imaging of monocyte precursors and monocytes/macrophages, or for in vitro immunostaining for immunoassay and/or microscopy examination analysis of cells or tissues.

10. The composition according to claim 4, further comprising a drug molecule.

11. The composition according to claim 10, wherein the composition is used for targeted drug delivery to immune cells.

12. The composition according to claim 11, wherein the composition is used for targeted drug delivery to monocyte precursors and monocytes/macrophages, and pulmonary macrophages.

13. A method for in vivo targeting immune cells, comprising administering an effective amount of the composition according to claim 4 to a subject in need thereof.

14. The method according to claim 13, wherein the composition is administered via subcutaneous injection, intravenous injection, intramuscular injection or pulmonary inhalation.

* * * * *

SEQUENCE LISTING

```
<160> NUMBER OF SEQ ID NOS: 39

<210> SEQ ID NO 1
<211> LENGTH: 8
<212> TYPE: PRT
<213> ORGANISM: Homo sapiens

<400> SEQUENCE: 1

Ala Ile Leu Glu Val Leu Gln Ser
1               5

<210> SEQ ID NO 2
<211> LENGTH: 10
<212> TYPE: PRT
<213> ORGANISM: Homo sapiens

<400> SEQUENCE: 2

Leu Arg Ala Ile Leu Glu Val Leu Gln Ser
1               5                   10
```

<210> SEQ ID NO 3
<211> LENGTH: 11
<212> TYPE: PRT
<213> ORGANISM: Homo sapiens

<400> SEQUENCE: 3

Ile Leu Arg Ala Ile Leu Glu Val Leu Gln Ser
1               5                   10

<210> SEQ ID NO 4
<211> LENGTH: 13
<212> TYPE: PRT
<213> ORGANISM: Homo sapiens

<400> SEQUENCE: 4

Ala Ala Ile Leu Arg Ala Ile Leu Glu Val Leu Gln Ser
1               5                   10

<210> SEQ ID NO 5
<211> LENGTH: 23
<212> TYPE: PRT
<213> ORGANISM: Homo sapiens

<400> SEQUENCE: 5

Glu Gln Pro Asp Pro Gly Ala Val Ala Ala Ala Ile Leu Arg Ala
1               5                   10                  15

Ile Leu Glu Val Leu Gln Ser
            20

<210> SEQ ID NO 6
<211> LENGTH: 19
<212> TYPE: PRT
<213> ORGANISM: Homo sapiens

<400> SEQUENCE: 6

Pro Gly Ala Val Ala Ala Ala Ala Ile Leu Arg Ala Ile Leu Glu Val
1               5                   10                  15

Leu Gln Ser

<210> SEQ ID NO 7
<211> LENGTH: 42
<212> TYPE: PRT
<213> ORGANISM: Homo sapiens

<400> SEQUENCE: 7

Thr Lys Asn Met Glu Ala Gly Ala Gly Arg Ala Ser Tyr Ile Ser Ser
1               5                   10                  15

Ala Arg Leu Glu Gln Pro Asp Pro Gly Ala Val Ala Ala Ala Ala Ile
            20                  25                  30

Leu Arg Ala Ile Leu Glu Val Leu Gln Ser
        35                  40

<210> SEQ ID NO 8
<211> LENGTH: 8
<212> TYPE: PRT
<213> ORGANISM: Artificial Sequence
<220> FEATURE:
<223> OTHER INFORMATION: Synthesized

<400> SEQUENCE: 8

Ala Val Leu Glu Val Leu Gln Gly
1               5

```
<210> SEQ ID NO 9
<211> LENGTH: 11
<212> TYPE: PRT
<213> ORGANISM: Artificial Sequence
<220> FEATURE:
<223> OTHER INFORMATION: Synthesized

<400> SEQUENCE: 9

Val Leu Arg Ala Val Leu Glu Val Leu Gln Gly
1               5                   10

<210> SEQ ID NO 10
<211> LENGTH: 23
<212> TYPE: PRT
<213> ORGANISM: Artificial Sequence
<220> FEATURE:
<223> OTHER INFORMATION: Synthesized

<400> SEQUENCE: 10

Glu Gln Pro Asp Pro Ser Ala Val Ala Ala Ala Ala Ile Leu Arg Ala
1               5                   10                  15

Ile Leu Glu Val Leu Gln Gly
            20

<210> SEQ ID NO 11
<211> LENGTH: 23
<212> TYPE: PRT
<213> ORGANISM: Artificial Sequence
<220> FEATURE:
<223> OTHER INFORMATION: Synthesized

<400> SEQUENCE: 11

Leu Gln Pro Asp Pro Ser Ala Val Ala Ala Ala Ala Val Leu Arg Ala
1               5                   10                  15

Val Leu Glu Val Leu Gln Gly
            20

<210> SEQ ID NO 12
<211> LENGTH: 23
<212> TYPE: PRT
<213> ORGANISM: Gallus gallus

<400> SEQUENCE: 12

Leu Gln Pro Asp Pro Gly Ala Val Ala Ala Ala Ala Val Leu Arg Ala
1               5                   10                  15

Val Leu Glu Gly Leu Gln Gly
            20

<210> SEQ ID NO 13
<211> LENGTH: 26
<212> TYPE: PRT
<213> ORGANISM: Rattus norvegicus

<400> SEQUENCE: 13

Asp Gln Pro Asp Pro Gly Ala Val Ala Ala Ala Ala Ile Phe Arg Ala
1               5                   10                  15

Ile Leu Glu Val Leu Gln Thr Lys Ala Ala
            20                  25

<210> SEQ ID NO 14
<211> LENGTH: 26
<212> TYPE: PRT
<213> ORGANISM: Canis lupus
```

```
<400> SEQUENCE: 14

Asp Gln Pro Asp Pro Gly Ala Val Ala Ala Ala Ile Leu Arg Thr
1               5                   10                  15

Ile Leu Glu Val Leu Gln Ser Gln Gly Val
            20                  25

<210> SEQ ID NO 15
<211> LENGTH: 26
<212> TYPE: PRT
<213> ORGANISM: Sus scrofa

<400> SEQUENCE: 15

Asp Gln Pro Asp Pro Gly Ala Val Ala Ala Ala Ile Leu Arg Ala
1               5                   10                  15

Ile Leu Glu Val Leu Gln Ser Gln Gly Ala
            20                  25

<210> SEQ ID NO 16
<211> LENGTH: 23
<212> TYPE: PRT
<213> ORGANISM: Macaca mulatta

<400> SEQUENCE: 16

Glu Gln Pro Asp Pro Gly Ala Val Ala Ala Ala Ile Leu Arg Ala
1               5                   10                  15

Ile Leu Glu Val Leu Gln Ser
            20

<210> SEQ ID NO 17
<211> LENGTH: 26
<212> TYPE: PRT
<213> ORGANISM: Mus musculus

<400> SEQUENCE: 17

Asp Gln Pro Asp Pro Gly Ala Val Ala Ala Ala Ile Phe Arg Ala
1               5                   10                  15

Ile Leu Glu Val Leu Gln Thr Gln Gly Ala
            20                  25

<210> SEQ ID NO 18
<211> LENGTH: 26
<212> TYPE: PRT
<213> ORGANISM: Bos taurus

<400> SEQUENCE: 18

Asp Gln Pro Asp Pro Gly Ala Val Ala Ala Ala Ile Leu Arg Ala
1               5                   10                  15

Ile Leu Glu Val Leu Gln Ser Gln Gly Ala
            20                  25

<210> SEQ ID NO 19
<211> LENGTH: 41
<212> TYPE: PRT
<213> ORGANISM: Saimiri boliviensis

<400> SEQUENCE: 19

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ile Leu
            20                  25                  30
```

-continued

Arg Ala Ile Leu Glu Val Leu Gln Ser
        35                  40

<210> SEQ ID NO 20
<211> LENGTH: 41
<212> TYPE: PRT
<213> ORGANISM: Aotus nancymaae

<400> SEQUENCE: 20

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 21
<211> LENGTH: 41
<212> TYPE: PRT
<213> ORGANISM: Callithrix jacchus

<400> SEQUENCE: 21

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 22
<211> LENGTH: 41
<212> TYPE: PRT
<213> ORGANISM: Cebus capucinus

<400> SEQUENCE: 22

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 23
<211> LENGTH: 41
<212> TYPE: PRT
<213> ORGANISM: Cercocebus atys

<400> SEQUENCE: 23

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 24
<211> LENGTH: 41
<212> TYPE: PRT
<213> ORGANISM: Chlorocebus sabaeus

<400> SEQUENCE: 24

-continued

```
Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 25
<211> LENGTH: 41
<212> TYPE: PRT
<213> ORGANISM: Colobus angolensis

<400> SEQUENCE: 25

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 26
<211> LENGTH: 41
<212> TYPE: PRT
<213> ORGANISM: Homo sapiens

<400> SEQUENCE: 26

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 27
<211> LENGTH: 41
<212> TYPE: PRT
<213> ORGANISM: Macaca fascicularis

<400> SEQUENCE: 27

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 28
<211> LENGTH: 41
<212> TYPE: PRT
<213> ORGANISM: Macaca mulatta

<400> SEQUENCE: 28

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 29
```

```
<211> LENGTH: 41
<212> TYPE: PRT
<213> ORGANISM: Macaca nemestrina

<400> SEQUENCE: 29

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 30
<211> LENGTH: 41
<212> TYPE: PRT
<213> ORGANISM: Mandrillus leucophaeus

<400> SEQUENCE: 30

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 31
<211> LENGTH: 41
<212> TYPE: PRT
<213> ORGANISM: Nomascus leucogenys

<400> SEQUENCE: 31

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 32
<211> LENGTH: 41
<212> TYPE: PRT
<213> ORGANISM: Oryctolagus cuniculus

<400> SEQUENCE: 32

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 33
<211> LENGTH: 41
<212> TYPE: PRT
<213> ORGANISM: Pan paniscus

<400> SEQUENCE: 33

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30
```

Arg Ala Ile Leu Glu Val Leu Gln Ser
        35                  40

<210> SEQ ID NO 34
<211> LENGTH: 41
<212> TYPE: PRT
<213> ORGANISM: Pan troglodytes

<400> SEQUENCE: 34

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 35
<211> LENGTH: 41
<212> TYPE: PRT
<213> ORGANISM: papio anubis

<400> SEQUENCE: 35

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 36
<211> LENGTH: 41
<212> TYPE: PRT
<213> ORGANISM: Pongo abelii

<400> SEQUENCE: 36

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 37
<211> LENGTH: 41
<212> TYPE: PRT
<213> ORGANISM: Rhinopithecus bieti

<400> SEQUENCE: 37

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
            20                  25                  30

Arg Ala Ile Leu Glu Val Leu Gln Ser
        35                  40

<210> SEQ ID NO 38
<211> LENGTH: 41
<212> TYPE: PRT
<213> ORGANISM: Rhinopithecus roxellana

<400> SEQUENCE: 38

```
Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ala Ile Leu
                20                  25                  30

Arg Ala Ile Leu Glu Val Leu Gln Ser
        35                  40

<210> SEQ ID NO 39
<211> LENGTH: 9
<212> TYPE: PRT
<213> ORGANISM: Artificial Sequence
<220> FEATURE:
<223> OTHER INFORMATION: Synthesized

<400> SEQUENCE: 39

Ala Ile Leu Glu Val Leu Gln Ser Lys
1               5
```